US012612498B2

(12) United States Patent
Enomoto et al.

(10) Patent No.: US 12,612,498 B2
(45) Date of Patent: *Apr. 28, 2026

(54) METAL-RESIN COMPOSITE AND USE THEREOF

(71) Applicant: NIPPON STEEL Chemical & Material Co., Ltd., Tokyo (JP)

(72) Inventors: Yasushi Enomoto, Tokyo (JP); Yasufumi Matsumura, Tokyo (JP)

(73) Assignee: NIPPON STEEL Chemical & Material Co., Ltd., Tokyo (JP)

( * ) Notice: Subject to any disclaimer, the term of this patent is extended or adjusted under 35 U.S.C. 154(b) by 884 days.

This patent is subject to a terminal disclaimer.

(21) Appl. No.: 16/474,549

(22) PCT Filed: Dec. 25, 2017

(86) PCT No.: PCT/JP2017/046393

§ 371 (c)(1),
(2) Date: Jun. 28, 2019

(87) PCT Pub. No.: WO2018/123952

PCT Pub. Date: Jul. 5, 2018

(65) Prior Publication Data

US 2019/0367694 A1      Dec. 5, 2019

(30) Foreign Application Priority Data

Dec. 28, 2016      (JP) ................................. 2016-256913

(51) Int. Cl.
G01N 33/543      (2006.01)
C08J 7/12      (2006.01)
(Continued)

(52) U.S. Cl.
CPC .................. C08J 7/12 (2013.01); C08K 3/08 (2013.01); G01N 33/54313 (2013.01);
(Continued)

(58) Field of Classification Search
CPC ........... C08J 7/12; C08J 2300/20; C08K 3/08; C08K 2003/0831; C08K 2201/005;
(Continued)

(56) References Cited

U.S. PATENT DOCUMENTS 5,248,772 A      9/1993 Siiman et al.
10,690,665 B2 *    6/2020 Matsumura ...... G01N 33/54346
(Continued)

FOREIGN PATENT DOCUMENTS

CN      102474023      5/2012
CN      102597012      7/2012
(Continued)

OTHER PUBLICATIONS

Murugan et al. ("Synthesis, Characterization, and Heterogeneous Catalysis of Polymer-Supported Poly(propyleneimine) Dendrimer Stabilized Gold Nanoparticle Catalyst," Journal of Polymer Science: Part A: Polymer Chemistry, vol. 48, pp. 2525-2532, published 2010). (Year: 2010).*

(Continued)

*Primary Examiner* — Shafiqul Haq
*Assistant Examiner* — Nam P Nguyen
(74) *Attorney, Agent, or Firm* — JCIP GLOBAL INC.

(57)      ABSTRACT

A metal-resin composite that has a structure in which a plurality of metal particles are fixed to resin particles and, in the range of pH 3 to pH 10, the maximum value of the zeta potential is at least 5 mV and the minimum value is −5 mV or less. In this metal-resin composite, it is preferable that, in the range of pH 3 to pH 10, the difference between the maximum value and the minimum value of the zeta potential is at least 20 mV; and it is further preferable that the point of zero charge of the zeta potential is in the range of pH 3.5 to pH 9.0. This metal-resin composite can be used in immunoassays and in immunoassay reagents as a labeled (Continued)

substance by making antigens or antibodies adhere to the surface of the metal-resin composite.

15 Claims, 3 Drawing Sheets

(51) Int. Cl.

| | |
|---|---|
| *C08K 3/08* | (2006.01) |
| *G01N 33/545* | (2006.01) |
| *G01N 33/553* | (2006.01) |
| *B82Y 30/00* | (2011.01) |
| *B82Y 40/00* | (2011.01) |

(52) U.S. Cl.
CPC ......... *G01N 33/545* (2013.01); *G01N 33/553* (2013.01); *B82Y 30/00* (2013.01); *B82Y 40/00* (2013.01); *C08J 2300/20* (2013.01); *C08K 2003/0831* (2013.01); *C08K 2201/005* (2013.01)

(58) Field of Classification Search
CPC ........... G01N 33/54313; G01N 33/545; G01N 33/553; G01N 33/543; G01N 21/41; G01N 33/585; B82Y 30/00; B82Y 40/00
See application file for complete search history.

(56) References Cited

U.S. PATENT DOCUMENTS

| | | | | |
|---|---|---|---|---|
| 11,215,611 B2 * | 1/2022 | Matsumura | ...... | G01N 33/54388 |
| 11,366,112 B2 * | 6/2022 | Matsumura | .......... | G01N 33/553 |
| 11,733,241 B2 * | 8/2023 | Matsumura | ...... | G01N 33/54346 435/6.19 |
| 2006/0188932 A1 * | 8/2006 | Oka | ................... | G01N 33/5434 435/7.1 |
| 2010/0298536 A1 * | 11/2010 | Park | ..................... | A61K 49/085 977/773 |
| 2013/0045877 A1 | 2/2013 | Yap et al. | | |
| 2014/0031195 A1 * | 1/2014 | Sakurai | ................... | B01J 23/66 502/344 |
| 2015/0064718 A1 | 3/2015 | Caracci et al. | | |
| 2017/0168049 A1 * | 6/2017 | Matsumura | ...... | G01N 33/54388 |

FOREIGN PATENT DOCUMENTS

| | | |
|---|---|---|
| CN | 102951603 | 3/2013 |
| CN | 105324667 | 2/2016 |
| CN | 105324668 | 2/2016 |
| CN | 105548307 | 5/2016 |
| EP | 1496363 | 1/2005 |
| EP | 2543694 | 1/2013 |
| JP | H03206959 | 9/1991 |
| JP | H05010950 | 1/1993 |
| JP | 2003262638 | 9/2003 |
| JP | 2004226395 | 8/2004 |
| JP | 2009168495 | 7/2009 |
| JP | 2009227883 | 10/2009 |
| JP | 2011117906 | 6/2011 |
| JP | 2012177691 | 9/2012 |
| JP | 2015068764 | 4/2015 |
| TW | 201625948 | 7/2016 |
| WO | 9315117 | 8/1993 |
| WO | 2014203614 | 12/2014 |
| WO | 2015022914 | 2/2015 |
| WO | 2016002742 | 1/2016 |
| WO | 2016002743 | 1/2016 |
| WO | 2017010391 | 1/2017 |

OTHER PUBLICATIONS

Kanahara et al., "Fabrication of gold nanoparticle-polymer composite particles with raspberry, core-shell and amorphous morphologies at room temperature via electrostatic interactions and diffusion," Soft Matter, Jan. 14, 2014, vol. 10, issue 2, pp. 275-280; first published on Oct. 11, 2013 (Year: 2013).*
"Search Report of Europe Counterpart Application", issued on Jul. 23, 2020, p. 1-p. 9.
"Office Action of Japan Counterpart Application" with English translation thereof, issued on Oct. 26, 2021, p. 1-p. 8.
Kensuke Akamatsu, et al., "Synthesis of pH-Responsive Nanocomposite Microgels with Size-Controlled Gold Nanoparticles from Ion-Doped, Lightly Cross-Linked Poly(vinylpyridine)," Langmuir, American Chemical Society, Oct. 9, 2009, pp. 1254-1259.
"International Search Report (Form PCT/ISA/210) of PCT/JP2017/046393," mailed on Apr. 3, 2018, with English translation thereof, pp. 1-4.
"Office Action of Taiwan Counterpart Application", issued on Jul. 16, 2021, with English translation thereof, p. 1-p. 11.
"Office Action of China Counterpart Application" with English translation thereof, issued on Oct. 29, 2021, p. 1-p. 15.
"Office Action of Japan Counterpart Application" with English translation thereof, issued on Jul. 5, 2022, p. 1-p. 4.
"Office Action of Korea Counterpart Application" with English translation thereof, issued on Jun. 23, 2022, p. 1-p. 9.
"Decision of Rejection of China Counterpart Application" with English translation thereof, issued on Jul. 27, 2022, p. 1-p. 15.
"Office Action of Europe Counterpart Application, Application No. 17886839.4", issued on Dec. 5, 2022, p. 1-p. 7.
"Notification of Reexamination of China Counterpart Application", with English translation thereof, issued on Aug. 6, 2025, pp. 1-19.
"Reexamination Decision of China Counterpart Application", with English translation thereof, issued on Sep. 25, 2025, pp. 1-38.

* cited by examiner

METAL-RESIN COMPOSITE AND USE THEREOF

CROSS-REFERENCE TO RELATED APPLICATION

This application is a 371 application of the international PCT application serial no. PCT/JP2017/046393, filed on Dec. 25, 2017, which claims the priority benefit of Japan application no. 2016-256913, filed on Dec. 28, 2016. The entirety of each of the above-mentioned patent applications is hereby incorporated by reference herein and made a part of this specification.

TECHNICAL FIELD

The present invention relates to, for example, a metal-resin composite that can be preferably used for applications such as immunological measurement, a labeling substance using the same, an immunoassay, a reagent for immunological measurement, an analyte measurement method, an analyte measurement kit, and a test strip for lateral flow chromatography.

BACKGROUND ART

Since there are numerous chemical substances in a living body, a technique for qualitatively and quantitatively analyzing specific trace components in a living body is very important. In the fields of medicine, pharmaceuticals, health foods, biotechnology, the environment, and the like, chemicals and foods that act only in specific parts (chemical substances) in a living body, analysis devices and diagnostic agents for detecting small changes in a living body, and the like have been developed together with such techniques.

An immunoassay is one of the above analysis techniques. This is also called an immunological measurement method, and is a method of qualitatively and quantitatively analyzing a trace component using a specific reaction between an antigen and an antibody which is one of immunologic reactions. A reaction between an antigen and an antibody is widely used in the above fields because sensitivity and reaction selectivity are high. There are various measurement methods according to the measurement principles of immunoassay. For example, an enzyme immunoassay (EIA), a radioimmunoassay (RIA), a chemiluminescence immunoassay (CLIA), a fluorescence immunoassay (FIA), a latex agglutination method (LIA, PA), immunochromatography (ICA), a hemagglutination method (HA), a hemagglutination inhibition method (HI), and the like may be exemplified. In addition, physical and chemical measurement methods, biological measurement methods, and the like may be exemplified in addition to immunoassays.

In immunoassays, antigens or antibodies are qualitatively or quantitatively detected from a change (change in concentration of antigens, antibodies or composites) when antigens and antibodies react to form composites. When these are detected, if a labeling substance binds to antibodies, antigens, or composites, the detection sensitivity increases.

Therefore, a labeling ability of the labeling substance is an important factor that affects a detection ability in the immunoassay. In the immunoassays exemplified above, an erythrocyte (in the case of HA), latex particles (in the case of LIA), a fluorescent dye (in the case of FIA), a radioactive element (in the case of RIA), an enzyme (in the case of EIA), a chemiluminescent substance (in the case of CLIA), and the like are used as the labeling substance.

Incidentally, when colored fine particles are used as a labeling substance, since it is possible to visually confirm that a change is detected without using a special analysis device, more convenient measurement is expected. Examples of such colored fine particles include colloidal particles of metals and metal oxides, and latex particles colored with a dye (for example, Patent Literature 1, and Patent Literature 4). However, since a color tone of the colloidal particles is determined according to the particle size and preparation conditions, there is a problem in that it is difficult to obtain a desired vivid and dark color tone, that is, visibility is insufficient.

In addition, colored latex particles have a problem in that an effect of coloring with a dye is weak, and visual determination is insufficient. Here, when an amount of coloring dye is increased in order to address this problem, since the dye covers the surface of the latex and an original state of the surface of the latex particles is impaired, there is a problem in that it may be difficult to bind antigens or antibodies. In addition, there is a problem in that clogging of pores of a chromatographic medium such as a membrane filter and nonspecific aggregation of latex particles to increase a coloring material of a dye for dark coloring does not necessarily result in improvement in performance.

An immunochromatographic method in which, in order to improve visibility of the above labeling substance, an antibody (labeled antibody) to which the labeling substance is bound reacts with an antigen to form a composite, another metal is then additionally modified with respect to these labeling substance, and thus the detection sensitivity of the labeling substance is amplified has been disclosed (Patent Literature 2 and 5). However, in this method, the operation is complicated and stable amplification is difficult. In addition, the measurement cost is high because a special device is necessary, and thus applicable applications and usage environments can be considered to be limited.

In addition, colored latex including gold nanoparticles bound to the surface of polymer latex particles has been disclosed (Patent Literature 3).

When gold nanoparticles are bound to the surface of polymer latex particles, the gold nanoparticles themselves are a colorant and contribute to improvement in visual determination and detection sensitivity. In addition, since the gold nanoparticles themselves have an excellent ability to bind to an antigen or an antibody, even if the gold nanoparticles are bound to an extent at which a sufficient dark color is obtained, a sufficient amount of antigen or antibody can be bound.

The colored latex is obtained by binding gold nanoparticles to the surface of the latex by emitting gamma rays to a dispersion of a styrene-acrylic acid copolymer latex and HAuCl which is a precursor of gold nanoparticles. However, in the colored latex, since gold nanoparticles are bound to only the surface of the latex, there is a limitation on a supported amount of gold nanoparticles at which surface plasmon resonance is exhibited, and the gold nanoparticles are likely to be detached. As a result, there is a risk of the visibility and sensitivity of a reagent for immunological measurement not being sufficient. In addition, since electromagnetic radiation such as gamma rays is emitted, there is a risk of the latex being damaged. In addition, in the specification in Patent Literature 3, preferable ranges of the diameter of the latex and the size of gold nanoparticles are disclosed. However, in the examples, almost no conditions suitable for implementation are disclosed, for example, it is not clear whether verification has been performed in such preferable ranges, and there is no basis for defining the preferable ranges.

In addition, in Patent Literature 4, polymer latex particles covered with a metal (gold) are disclosed, and an application to a reagent that can be used for a microscopic examination and an immunoassay method is suggested.

However, in the polymer latex particles covered with the metal (gold), the material and the particle size of the polymer latex particles are not disclosed. In addition, there is no verification regarding an effect of a reagent that can be used for an immunoassay method. Therefore, the effect of a reagent in the metal (gold) and polymer latex particles is unknown.

In addition, in Non-Patent Literature 1, a microgel in which gold nanoparticles are supported on poly-2-vinylpyridine latex particles is disclosed. The pH responsiveness of the particle size of the microgel is confirmed from a change in movement of localized surface plasmon resonance of the gold nanoparticles. However, in the microgel, the gold nanoparticles are supported on a single layer near the surface layer of the latex particles. Therefore, a supported amount of the gold nanoparticles is small and a dark color tone effective for an immunoassay cannot be considered to be obtained. In addition, the material, the structure, the composition and the like of the microgel have not been studied, and an effect on a specific application such as a reagent for immunological measurement is unknown.

In addition, Patent Literature 5 discloses composite fine particles including metal core ultrafine particles and a polymer having a metal ion coordinating group and surrounding the metal core ultrafine particles, and applications to various fields such as a detection field of a diagnostic agent and the like are suggested. In addition, in examples, composite fine particles in which crosslinked fine particles of a vinylpyridine-divinylbenzene copolymer are surrounded with gold nanoparticles obtained by reducing chlorauric acid are disclosed. However, a detailed structure and physical properties of the composite fine particles have not been studied and an effect on a specific application such as a reagent for immunological measurement is unknown.

As described above, it is expected that latex particles with gold nanoparticles bound thereto or covered therewith will be able to be used as a reagent for immunological measurement. However, in the techniques of the related art, the durability and visibility are not sufficient. In addition, even when they have high visibility, applicable applications and usage environments are limited.

In view of the circumstances of the related art, the applicant has found and proposed previously a resin-metal composite in which metal particles with a specific proportion are present on the outer layer section of resin particles (for example, Patent Literature 6). The resin-metal composite has excellent durability and visibility, particularly, in applications of an immunological measurement material, and can perform highly sensitive determination without requiring addition of a special device and a work process.

CITATION LIST

Patent Literature

Patent Literature 1

Japanese Unexamined Patent Application Publication No. H5-10950

Patent Literature 2

Japanese Unexamined Patent Application Publication No. 2011-117906

Patent Literature 3

Japanese Unexamined Patent Application Publication No. 2009-168495

Patent Literature 4

Japanese Unexamined Patent Application Publication No. H3-206959

Patent Literature 5

Japanese Unexamined Patent Application Publication No. 2009-227883

Patent Literature 6

PCT International Publication No. WO2016/002742

Non-Patent Literature

Non-Patent Literature 1

K. Akamatsu, M. Shimada, T. Tsuruoka, H. Nawafune, S. Fujii and Y. Nakamura; Langmuir 2010, 26, 1254-1259.

SUMMARY OF THE INVENTION

Technical Problem

In order to use a metal-resin composite as a labeling substance in immunological measurement, it is necessary to stably bind it to a ligand such as an antigen and an antibody, a blocking agent, or the like. However, when a ligand is labeled with a metal-resin composite, even if a stable binding state can be formed, excellent detection sensitivity cannot always be obtained. For example, fine metal-resin composites are likely to aggregate. When aggregation occurs, not only handling properties significantly deteriorate, but also the concentration of the metal-resin composite which is a labeling substance may be non-uniform, and the detection sensitivity may be greatly reduced.

In addition, antigens, antibodies and blocking agents used for immunological measurement include various types of proteins, synthetic polymers, and low-molecular-weight compounds, and those having a strong anionic property (for example, casein), and those having a strong cationic property (for example, whey). Therefore, a labeling substance in which all of such antigens and antibodies can be used is particularly preferable due to cost reduction of materials.

The present invention provides a metal-resin composite in which aggregation is unlikely to occur when bound to a ligand such as an antigen and an antibody or a blocking agent, which has excellent handling properties, and also to which a plurality of types of antigen, antibody, and blocking agent can be applied, and provides, for example, a metal-resin composite for immunological measurement by which determination is possible with high sensitivity in immunological measurement.

Solution to Problem

The inventors conducted extensive studies, and as a result, found that it is possible to address the above problems by providing a metal-resin composite in which a plurality of metal particles are fixed to resin particles and of which a structure and electrical properties are controlled, and thereby completed the present invention.

Specifically, the metal-resin composite of the present invention is a metal-resin composite which includes resin particles and a plurality of metal particles that are fixed to the resin particle, and in which, in a range of pH 3 to pH 10, a maximum value of a zeta potential is 5 mV or higher and a minimum value thereof is −5 mV or lower.

In the metal-resin composite of the present invention, in a range of pH 3 to pH 10, a difference between the maximum value and the minimum value of the zeta potential may be 20 mV or higher.

In the metal-resin composite of the present invention, more preferably, a point of zero charge of the zeta potential is in a range of pH 3.5 to pH 9.0.

In the metal-resin composite of the present invention, the average particle size of the metal particles may be in a range of 1 nm to 100 nm.

In the metal-resin composite of the present invention, the average particle size thereof may be in a range of 30 nm to 1,000 nm.

In the metal-resin composite of the present invention, the resin particles may be polymer particles having a structure including a substituent to which metal ions are able to be adhered.

In the metal-resin composite of the present invention, the metal particles may be particles of gold, platinum, palladium, silver, nickel, copper, or an alloy thereof.

A labeling substance of the present invention includes any of the metal-resin composites. In this case, antigens or antibodies may be adhered to the surface of the metal-resin composite and used.

An immunoassay of the present invention uses any of the above labeling substances.

A reagent for immunological measurement of the present invention includes any of the above metal-resin composites.

An analyte measurement method of the present invention is a method for detecting or quantifying an analyte included in a sample. The analyte measurement method includes the following Processes (I) to (III) that are performed using a test strip for lateral flow chromatography that includes a membrane and a determination section in which a capture ligand that specifically binds to the analyte is fixed to the membrane.

Process (I): A process in which the analyte included in the sample is brought into contact with a labeled antibody obtained by labeling an antibody that specifically binds to the analyte with any of the above metal-resin composites Process (II): A process in which a composite including the analyte and the labeled antibody formed in Process (I) is brought into contact with the capture ligand in the determination section, and Process (III): A process in which a color development intensity derived from localized surface plasmon resonance and/or light energy absorption due to electron transition of the metal-resin composite is measured An analyte measurement kit of the present invention is an analyte measurement kit for detecting or quantifying an analyte included in a sample. The analyte measurement kit includes a test strip for lateral flow chromatography including a membrane and a determination section in which a capture ligand that specifically binds to the analyte is fixed to the membrane; and a detection reagent including an labeled antibody obtained by labeling an antibody that specifically binds to the analyte with any of the above metal-resin composites.

A test strip for lateral flow chromatography of the present invention is used to detect or quantify an analyte included in a sample. The test strip for lateral flow chromatography includes a membrane, a determination section in which a capture ligand that specifically binds to the analyte is fixed to the membrane in a direction in which the sample is developed; and a reaction section including a labeled antibody obtained by labeling an antibody that specifically binds to the analyte with any of the above metal-resin composites upstream from the determination section.

Advantageous Effects of Invention

Since the metal-resin composite of the present invention has a specific zeta potential, it can interact with various substances irrespective of whether they are anionic or cationic. Therefore, it has excellent dispersibility when bound to a plurality of types of ligand such as an antigen and an antibody, or a blocking agent, and aggregation is unlikely to occur. Here, the "zeta potential" refers to a potential of a sliding surface of an electric double layer formed around the metal-resin composite in an acidic solution or an alkaline solution, and is measured as a potential difference between an electrically neutral area that is sufficiently separated from the metal-resin composite and the sliding surface using, for example, an electrophoretic light scattering method.

In addition, since the metal-resin composite of the present invention has a structure in which a plurality of metal particles are fixed to resin particles, a supported amount of metal particles is large and the metal particles are less likely to be detached from the resin particles.

In addition, the metal particles also exhibit light energy absorption due to electron transition in addition to localized surface plasmon resonance.

Therefore, the metal-resin composite of the present invention has excellent handling properties, durability, visibility, visual determination, and detection sensitivity. Therefore, the metal-resin composite can be preferably applied for, for example, a labeling substance for immunological measurement such as EIA, RIA, CLIA, FIA, LIA, PA, ICA, HA, and HI, a reagent for immunological measurement, medicines, solid catalysts, dyes, paints, conductive materials, electrodes, and sensor elements. In particular, when the metal-resin composite of the present invention is used for immunological measurement, handling properties, durability and visibility are excellent, a nonspecific reaction is inhibited, there is no need to add a special device or a work process for various antigens and antibodies, and determination is possible with high sensitivity.

DESCRIPTION OF EMBODIMENTS

Figure 1:
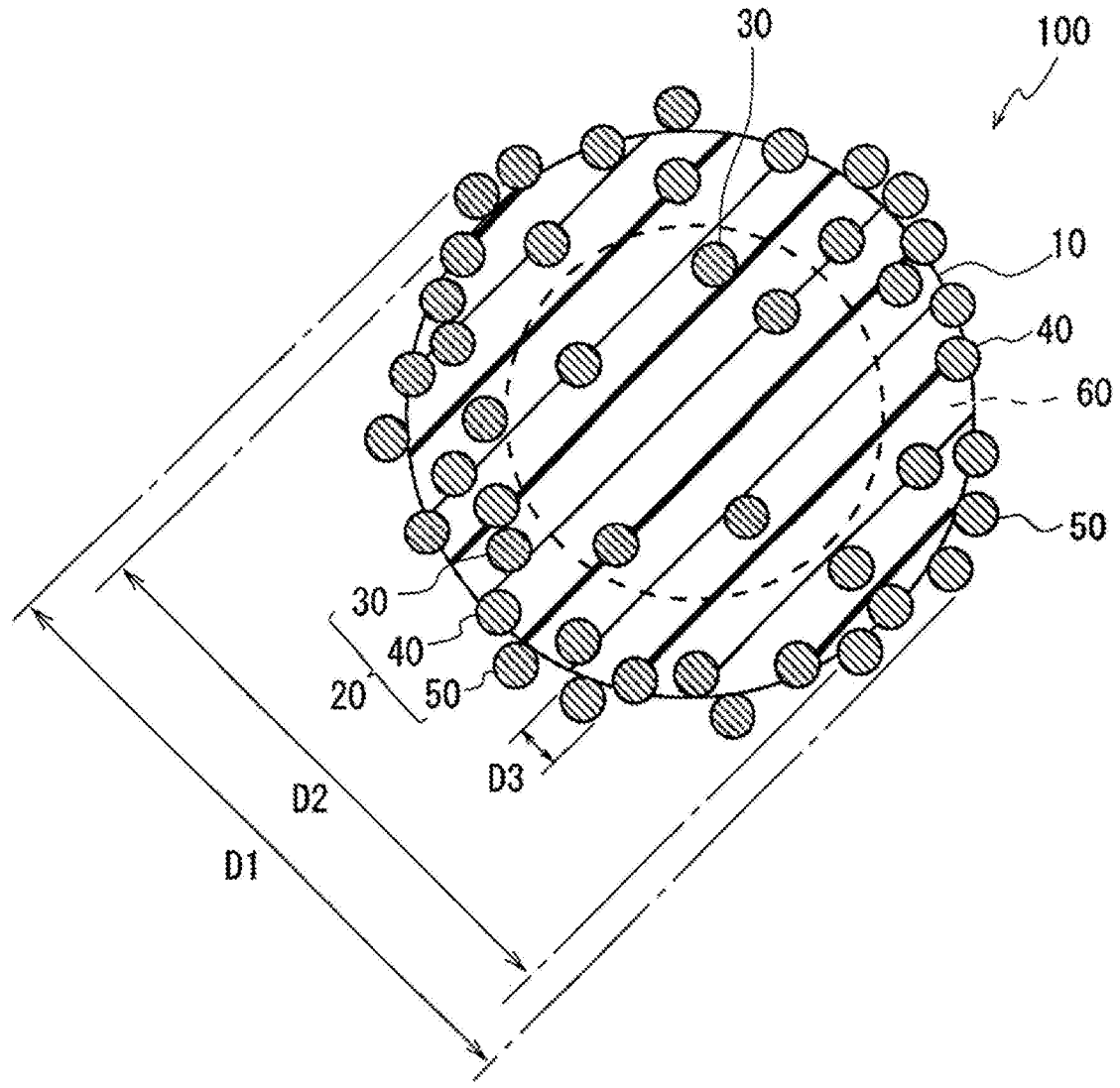
FIG. 1 is a schematic diagram showing a structure of a cross section of a metal-resin composite according to an embodiment of the present invention.

Embodiments of the present invention will be appropriately described below in detail with reference to the drawings. FIG. 1 is a cross-sectional schematic diagram of a metal-resin composite according to an embodiment of the present invention. A metal-resin composite 100 includes a resin particle 10 and metal particles 20. In the metal-resin composite 100, the metal particles 20 are fixed to the resin particle 10. The resin particle 10 is preferably a particle that is relatively larger than the metal particles 20. That is, in the metal-resin composite 100, a plurality of metal particles 20 that are relatively small are fixed to the large resin particle 10. In this case, as shown in FIG. 1, the relationships between a particle size D1 of the entire metal-resin composite 100, a particle size D2 of the resin particle 10, and a particle size D3 of the metal particles 20 is D1>D2>D3.

In addition, in the metal-resin composite 100, a dispersed state of the metal particles 20 in the resin particle 10 is not limited. For example, the metal particles 20 may be two-dimensionally distributed on the surface of the resin particle 10 and the metal particles 20 may be enclosed in the resin particle 10. As a former form, a plurality of metal particles 20 may be in contact with each other on the surface of the resin particle 10 to form a continuous film. In addition, as a latter form, a core-shell structure in which the resin particle 10 is a shell and the metal particle 20 is a core may be formed. In addition, some of the metal particles 20 may be three-dimensionally distributed on an outer layer section 60 of the resin particle 10. In this case, some of the metal particles 20 that are three-dimensionally distributed may be partially exposed to the outside of the resin particle 10 and the remaining metal particles 20 may be enclosed in the resin particle 10. Specifically, as shown in FIG. 1, preferably, the metal particles 20 include metal particles that are completely enclosed in the resin particle 10 (hereinafter referred to as "enclosed particles 30"), metal particles having a portion that is embedded in the resin particle 10 and a portion that is exposed to the outside of the resin particle 10 (hereinafter referred to as "partially exposed particles 40"), and metal particles that are adhered to the surface of the resin particle 10 (hereinafter referred to as "surface-adhered particles 50").

For example, when the metal-resin composite 100 is used as a labeling substance for immunological measurement or a reagent for immunological measurement, an antigen, an antibody or a blocking agent is fixed to the surface of the resin particle 10 or the surface of the partially exposed particles 40 or the surface-adhered particles 50 and used. In this case, it is conceived that the antigen, antibody or blocking agent is fixed to the partially exposed particles 40 and the surface-adhered particles 50, but it is unlikely to be fixed to the enclosed particles 30. However, all of the partially exposed particles 40, the surface-adhered particles 50 and the enclosed particles 30 exhibit light energy absorption due to electron transition in addition to localized surface plasmon resonance. Therefore, not only the partially exposed particles 40 and the surface-adhered particles 50 but also the enclosed particles 30 contribute to improvement of visibility of a labeling substance for immunological measurement and a reagent for immunological measurement. Further, because the partially exposed particles 40 and the enclosed particles 30 have a larger area that is in contact with the resin particle 10 than the surface-adhered particles 50 and exhibit an anchor effect due to the embedded state, they have a strong physical adhesion force and are not easily detached from the resin particle 10. In addition, the antigen, antibody, or blocking agent adhered to the partially exposed particles 40 or the surface-adhered particles 50 is not easily detached because it is coordination bonded to a metal. Therefore, the durability and stability of a labeling substance for immunological measurement and a reagent for immunological measurement using the metal-resin composite 100 can be improved.

A case in which the metal-resin composite 100 is applied as a labeling substance for immunological measurement (hereinafter simply referred to as a "labeling substance") or a reagent for immunological measurement (hereinafter simply referred to as a "reagent") will be exemplified below.

In a range of pH 3 to pH 10, the metal-resin composite 100 has a maximum value of a zeta potential of 5 mV or higher and a minimum value of −5 mV or lower (first characteristic). When the zeta potential is in this range, in an acidic environment (for example, when dispersed in a dispersion medium having a pH of less than 7), the metal-resin composite 100 has a cationic functional group on the surface of the composite and is positively charged. On the other hand, in a basic environment (for example, when dispersed in a dispersion medium having a pH of higher than 7), the metal-resin composite 100 has an anionic functional group on the surface of the composite and is negatively charged. That is, when the antigen, antibody, or blocking agent is bound to the surface of the metal-resin composite 100, according to a pH of the dispersion medium (binding buffer), a surface charge state is suitable for binding to the antigen, antibody or blocking agent. Specifically, in an acidic environment, it can bind to a strongly anionic antigen or antibody, and in a basic environment, it can bind to a strongly cationic antigen or antibody. That is, the metal-resin composite 100 can stably bind to any antigen or antibody regardless of whether it is anionic or cationic. Therefore, the durability, stability, and versatility of a labeling substance for immunological measurement and a reagent for immunological measurement are high.

On the other hand, when the maximum value of the zeta potential is less than 5 mV or the minimum value exceeds −5 mV, the dispersibility due to electrostatic repulsion of the metal-resin composite 100 is poor and the metal-resin composite 100 itself is likely to aggregate. Therefore, handling of a labeling substance for immunological measurement and a reagent for immunological measurement is difficult and disadvantageous.

In this regard, a higher maximum value of the zeta potential is preferable and a smaller minimum value is preferable. The maximum value of the zeta potential is preferably 10 mV or higher and more preferably 20 mV or higher. In addition, the minimum value of the zeta potential is preferably −10 mV or lower and more preferably −20 mV or lower. In addition, for the same reason, in a range of pH 3 to pH 10, in the metal-resin composite 100, a difference between the maximum value and the minimum value of the zeta potential is preferably 20 mV or higher (second characteristic). The difference is more preferably 40 mV or higher and most preferably 60 mV or higher.

In addition, in the metal-resin composite 100, the point of zero charge of the zeta potential is preferably in a range of pH 3.5 to pH 9.0 (third characteristic). Here, the point of zero charge is a point at which the zeta potential is neither much above nor below zero. When the point of zero charge is in this range, in a weakly acidic to weakly basic environment in which a molecular biochemical reaction generally occurs, the surface charge of the metal-resin composite 100 can be put in a charge state in which both positive and negative polarities are large, and is preferable. In particular, in addition to the first characteristic and the second characteristic, when the third characteristic is additionally satisfied, in a range of pH 3.5 to pH 9.0, since this indicates that the zeta potential has greatly changed from the positive side to the negative side or from the negative side to the positive side, excellent dispersibility can be exhibited in a wide pH range of both an acidic environment having weak acidity and a basic environment having weak basicity.

On the other hand, when the point of zero charge is outside the range, there is a tendency that the charge state with both positive and negative polarities can be obtained only in a relatively strongly acidic or strongly basic environment.

In the metal-resin composite 100, the entire surfaces of the enclosed particles 30 are covered with a resin constituting the resin particle 10. In addition, in the partially exposed particles 40, a surface area of 5% or more and less than 100% is covered with a resin constituting the resin particle 10. In consideration of the durability of a labeling substance for immunological measurement and a reagent for immunological measurement, a lower limit thereof is preferably 20% or more of the surface area and more preferably 30% or more. In addition, in the surface-adhered particles 50, a surface area of more than 0% and less than 5% is preferably covered with a resin constituting the resin particle 10.

In addition, an amount of the metal particles 20 (a sum of the enclosed particles 30, the partially exposed particles 40 and the surface-adhered particles 50) supported on the metal-resin composite 100 is preferably 3 wt % to 80 wt % with respect to the weight of the metal-resin composite 100. In such a range, the metal-resin composite 100 has excellent visibility, and visual determination and detection sensitivity as a labeling substance. When an amount of the metal particles 20 supported thereon is less than 3 wt %, since an amount of antibodies or antigens that are fixed is small, the detection sensitivity tends to decrease. On the other hand, when an amount of the metal particles 20 supported thereon exceeds 80 wt %, the particle size of the metal particles 20 significantly increases and light absorption characteristics due to the metal particles 20 tend to deteriorate. An amount of the metal particles 20 supported thereon is more preferably 15 wt % to 70 wt %, and most preferably 15 wt % to 60 wt %.

In addition, 10 wt % to 90 wt % of the metal particles 20 are preferably the partially exposed particles 40 and the surface-adhered particles 50. In such a range, since a sufficient amount of antibodies or antigens fixed to the metal particles 20 can be secured, the sensitivity as a labeling substance is high. More preferably, 20 wt % to 80 wt % of the metal particles 20 are the partially exposed particles 40 and the surface-adhered particles 50, and in consideration of the durability of a labeling substance for immunological measurement and a reagent for immunological measurement, most preferably, the surface-adhered particles 50 make up 20 wt % or less.

In addition, when the metal-resin composite 100 is used for immunological measurement, in order to obtain excellent detection sensitivity, 60 wt % to 100 wt %, preferably 75 to 100 wt %, and more preferably, 85 to 100 wt % are in the outer layer section 60, and more preferably, the metal particles 20 are in a range of the first 40% from the surface of the resin particle 10 in the particle radius in the depth direction. In addition, when 5 wt % to 90 wt % of the metal particles 20 in the outer layer section 60 are the partially exposed particles 40 or the surface-adhered particles 50, a sufficient amount of antibodies or antigens fixed to the metal particles 20 can be secured. This is preferable because the sensitivity of a labeling substance is then high. In other words, 10 wt % to 95 wt % of the metal particles 20 in the outer layer section 60 are preferably the enclosed particles 30.

Here, the "outer layer section" refers to a section in a range of the first 50% from the surface of the resin particle 10 in the particle radius in the depth direction based on the outmost position (that is, the protruding end of the partially exposed particles 40 or the surface-adhered particles 50) of the metal-resin composite 100. In addition, "distributed three-dimensionally" means that the metal particles 20 are dispersed not only in the planar direction in the resin particle 10 but also in the depth direction.

Figure 2A:
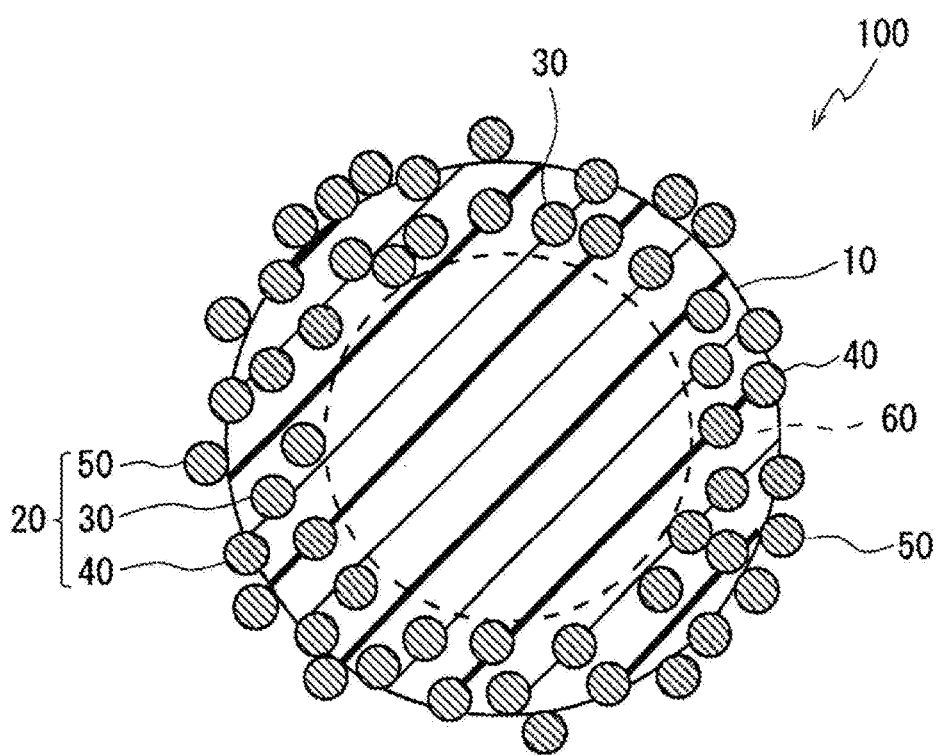
FIG. 2A is a schematic diagram showing a structure of a cross section of one embodiment of a metal-resin composite.

As described above, since the enclosed particles 30 also exhibit light energy absorption due to electron transition in addition to localized surface plasmon resonance, not only the partially exposed particles 40 and the surface-adhered particles 50 but also the enclosed particles 30 contribute to improvement of visibility of a labeling substance for immunological measurement and a reagent for immunological measurement. In consideration of such improvement of visibility, in the metal-resin composite 100, for example, as shown in FIG. 2A, preferably, the distribution of the enclosed particles 30 is concentrated in a certain range in the depth direction from the surface of the resin particle 10, and the enclosed particles 30 are not present near the center of the resin particle 10. More specifically, in order for light energy absorption due to electron transition in addition to localized surface plasmon resonance to be effectively exhibited by the enclosed particles 30, for example, when the particle size D2 of the resin particle 10 is 800 nm, 70 wt % or more, preferably 80 wt % or more, and more preferably 90 to 100 wt % of the enclosed particles 30 may be in, for example, a range of 0 to 200 nm, in the depth direction from the surface of the resin particle 10. In particular, when a region (enclosed particle distribution region) in which all of the enclosed particles 30 (100 wt %) are distributed is, for example, in a range of 0 to 100 nm, from the surface of the resin particle 10, this is preferable because it is then possible to maximize the light energy absorption exhibited due to electron transition in addition to localized surface plasmon resonance due to the enclosed particles 30.

Figure 2B:
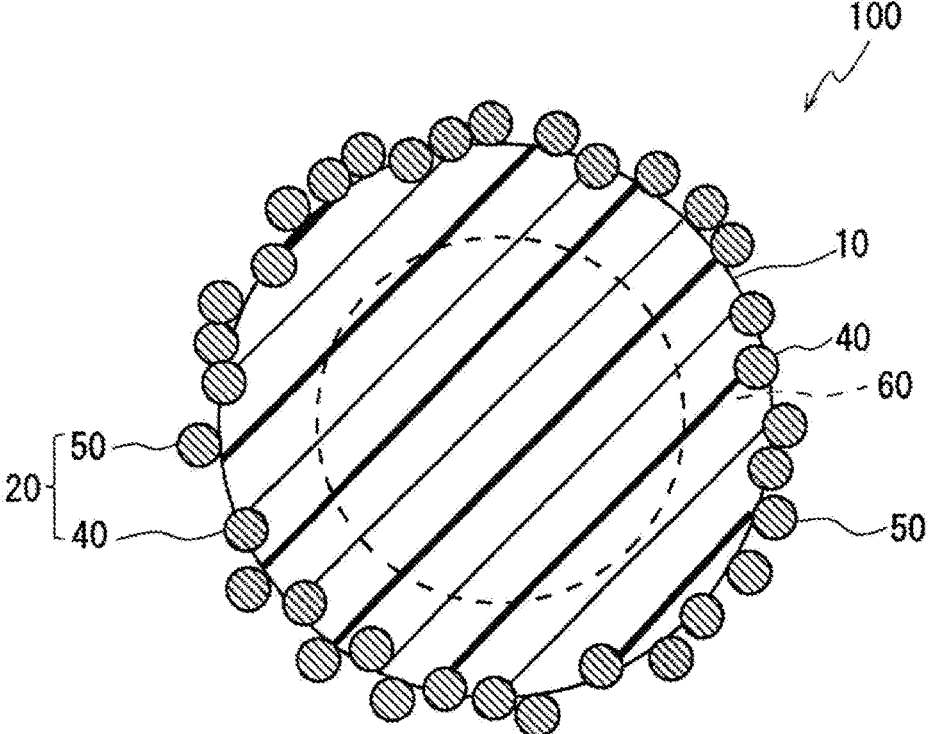
FIG. 2B is a schematic diagram showing a structure of a cross section of another embodiment of the metal-resin composite.

In addition, the metal-resin composite 100 may not include the enclosed particles 30. For example, as shown in FIG. 2B, in the metal-resin composite 100, all of the metal particles 20 may be fixed to the surface of the resin particle 10 without being superimposed in the radial direction of the resin particle 10. In this case, the metal particles 20 include the partially exposed particles 40 and the surface-adhered particles 50.

The structure or composition of the resin particle 10 is not limited, and a polymer particle having a structure including a substituent to which metal ions can be adhered is preferable. For example, a polymer to which anionic ions can be adhered may be exemplified. Regarding a polymer to which anionic ions can be adhered, a nitrogen-containing polymer is particularly preferable. Since nitrogen atoms in a nitrogen-containing polymer allow anionic ions such as $[AuCl_4]^-$, and $[PtCl_6]^{2-}$ which are precursors of the metal particles 20 that have excellent visibility and to which antigens or antibodies are easily fixed such that they are easily chemically attached thereto to be formed, they are preferable. In the present embodiment, in order to reduce the amount of metal ions adhered in the nitrogen-containing polymer to form the metal particles 20, some of the generated metal particles 20 may be made to become the enclosed particles 30 or the partially exposed particles 40. When $[AuCl_4]^-$ is used, gold particles are formed, and when $[PtCl_6]^{2-}$ is used, platinum particles are formed. In addition, anionic ions such as palladium, silver, nickel, and copper can also be used.

In addition, a polymer containing a carboxylic acid group such as an acrylic acid polymer and a polymer containing a sulfonic acid group such as polystyrene sulfonic acid (hereinafter collectively referred to as "a polymer to which cationic ions can be adhered") allow a cationic ion such as $Au^+$ or $Pt^{2+}$ to be chemically attached due to the contained carboxylic acid group and sulfonic acid group, and thus are preferable. For example, when chemically attached Au+ or $Pt^{2+}$ ions are reduced to form the metal particles 20 (in this case, gold particles or platinum particles), it is possible to provide the same structure as that of the nitrogen-containing polymer particle. In addition, cationic ions which are precursors of a metal such as palladium, silver, nickel, or copper can be used.

Here, since the polymer to which anionic ions can be adhered is cationic, it makes a zeta potential of the metal-resin composite 100 under an acidic environment positive. On the other hand, since a polymer to which cationic ions can be adhered is anionic, it makes a zeta potential under a basic environment of the metal-resin composite 100 negative.

On the other hand, regarding resin particles other than the nitrogen-containing polymer having a structure including a substituent to which metal ions can be adhered, for example, polystyrene, can be used. However, in this case, it is relatively difficult for the metal ions to be adhered to the inside of the resin. As a result, most of the generated metal particles 20 may be made to become the surface-adhered particles 50. As described above, since the surface-adhered particles 50 have a small area that is in contact with the resin particle 10, an adhesive strength between the resin and the metal is low, and the metal particles 20 are likely to be detached from the resin particle 10.

The nitrogen-containing polymer is a resin including nitrogen atoms in the main chain or side chain, and is, for example, a polyamine, polyamide, polypeptide, polyurethane, polyurea, polyimide, polyimidazole, polyoxazole, polypyrrole, or polyaniline, and preferably, a polyamine such as poly-2-vinylpyridine, poly-3-vinylpyridine, and poly-4-vinylpyridine. In addition, when there is a nitrogen atom in the side chain, for example, an acrylic resin, a phenolic resin, and an epoxy resin can be used generally.

In addition, the polymer to which cationic ions can be adhered is a resin including a carboxylic acid group, a sulfonic acid group, or the like in the main chain or side chain, and, for example, polyacrylic acid, vinyl carboxylate, polyvinyl acetate, polyvinyl sulfonic acid, and polystyrene sulfonic acid can be used generally.

The polymer to which anionic ions can be adhered and the polymer to which cationic ions can be adhered such as the nitrogen-containing polymer may be a copolymer with a known polymerizable monomer. Here, examples of the copolymer include a random copolymer, a block copolymer, an alternating copolymer, and a copolymer in which polymers are cross-linked. In addition, two or more types of monomers may be copolymerized to form the resin particle 10 and a monomer may be reacted with a functional group on the surface of the resin particle 10 and this may be further polymerized as a polymerization activated terminal. Although a copolymer composition thereof is not limited, there is preferably 10 mol % or more of a monomer including a substituent to which the metal ions can be adhered.

The polymerizable monomer can be selected according to applications of the metal-resin composite 100 without limitation. For example, in order to improve the shape of the resin particle 10, uniformity of the size and the dispersion stability, a polymerizable monomer having a characteristic as a surfactant can be used. Examples of such a polymerizable monomer include polyethylene glycol methyl ether methacrylate, and polyethylene glycol dimethacrylate.

In addition, when the resin particle 10 has a hydrolyzable group such as an ester bond, it may be partially hydrolyzed due to an acid treatment or an alkali treatment. Due to hydrolysis, since a group to which cationic ions can be adhered such as a carboxyl group is generated on the surface of the resin particle 10 and an effect of adhering metal ions is obtained, this is preferable. A known acid can be used as the acid. In order to increase an amount of a hydrolysis reaction, strongly acidic hydrochloric acid or sulfuric acid is preferable. A known alkali can be used as the alkali. In order to increase an amount of a hydrolysis reaction, a strongly alkaline potassium hydroxide or sodium hydroxide aqueous solution is preferable.

In addition, since the carboxyl group generated according to the hydrolysis is anionic, it makes a zeta potential of the metal-resin composite 100 under a basic environment negative. That is, when the resin particle 10 has a hydrolyzable group such as an ester bond, it is possible to control a zeta potential of the metal-resin composite 100 according to the hydrolysis.

In addition, in the metal-resin composite 100, the metal particles 20 are preferably gold, platinum, palladium, silver, nickel, copper, or an alloy thereof because a metal and a resin in a nano size are easily composited.

Such metals can be used alone or in a composite such as an alloy. Here, for example, a gold alloy refers to an alloy that includes gold and a type of metal other than gold, and includes 10 weight % or more of gold. In addition, for example, a platinum alloy refers to an alloy that includes platinum and a type of metal other than platinum, and includes 1 weight % or more of platinum.

When used as a labeling substance for immunological measurement and a reagent for immunological measurement, gold, platinum, and palladium which have excellent visibility and to which antigens or antibodies are easily fixed are more preferable. These are preferable because they exhibit absorption derived from localized surface plasmon resonance. Gold having a favorable storage stability or platinum that has an excellent detection sensitivity in immunological measurement is most preferable.

Compared to a metal-resin composite including particles of other types of metal, a platinum-resin composite in which platinum particles are used as metal particles is less likely to aggregate while it is bound to a ligand such as an antibody and has an excellent dispersibility which is significant. In addition, platinum particles are resistant to changes such as oxidation and have excellent storage stability. Further, the platinum particles exhibit absorption derived from localized surface plasmon resonance, for example, in a wide wavelength range of 250 nm to 900 nm, and also exhibit light energy absorption due to electron transition, and show strong development of a color close to black. Therefore, when the platinum-resin composite is used as a labeling substance, high visibility is obtained in immunological measurement and it is also possible to increase the detection sensitivity with respect to an analyte. In this case, when platinum particles are used, excellent detection sensitivity is obtained with a smaller supported amount than that with particles of another metal. Therefore, if the average particle size is the same, the platinum-resin composite is particularly preferable because it shows a significantly higher detection sensitivity than that of a resin composite including particles of another type of metal.

The platinum particles may include only platinum or may be an alloy including platinum and another metal. In a platinum alloy, other types of metal that form an alloy with platinum are not particularly limited, and, for example, silver, nickel, copper, gold, or palladium is preferable.

Compared to a metal-resin composite including particles of other types of metal, a gold-resin composite in which gold particles are used as metal particles is less likely to aggregate while it is bound to a ligand such as an antibody and has an excellent dispersibility which is significant. In addition, the visibility is excellent, and fixing to antigens or antibodies is easier. In particular, when the particle size of gold particles and an interparticle distance between gold particles are controlled, various colors such as red, purple, and blue can be developed. Therefore, when the gold-resin composite is used as a labeling substance for immunochromatography, it is possible to obtain labeling substances of various colors.

In addition, the average particle size of the metal particles 20 (that is, an average of the particle sizes D3 in FIG. 1) measured by observation under a scanning electron microscope (SEM) is preferably, for example, 1 to 100 nm. When the average particle size of the metal particles 20 is less than 1 nm or exceeds 100 nm, since localized surface plasmon resonance and light energy absorption due to electron transition are not easily exhibited, sensitivity tends to decrease.

When platinum particles are used as the metal particles 20, in order to obtain high detection sensitivity for a labeling substance for immunological measurement and a reagent for immunological measurement, the average particle size of platinum particles is preferably 1 nm or more and 50 nm or less, more preferably 1 nm or more and 30 nm or less, still more preferably 1 nm or more and 20 nm or less, and most preferably 1 nm or more and 15 nm or less. For example, if a platinum-resin composite having an average particle size of platinum particles of 15 nm or less is used as a labeling substance for immunochromatography, particularly excellent detection sensitivity can be obtained.

In addition, when gold particles are used as the metal particles 20, in order to obtain high detection sensitivity for a labeling substance for immunological measurement and a reagent for immunological measurement, the average particle size of gold particles is preferably 1 nm or more and less than 70 nm, and more preferably 1 nm or more and less than 50 nm.

In addition, the average particle size of the metal-resin composite 100 (that is, an average of the particle sizes D1 in FIG. 1) is, preferably, for example, 30 to 1,000 nm. When the average particle size of the metal-resin composite 100 is less than 30 nm, for example, since a supported amount of the metal particles 20 tends to decrease, coloration tends to be weaker than that of the metal particles 20 of the same size, and when the average particle size of the metal-resin composite 100 exceeds 1,000 nm, when it is used as a labeling substance or a reagent, it is likely to clog pores in a chromatographic medium such as a membrane filter and the dispersibility tends to decrease. In order to improve the dispersibility when it is used as a labeling substance or a reagent, and obtain high detection sensitivity when the metal-resin composite 100 is used for immunological measurement, the average particle size of the metal-resin composite 100 is preferably 100 nm or more and 700 nm or less, more preferably 250 nm or more and 650 nm or less, and most preferably 280 nm or more and 600 nm or less. In particular, if the average particle size of the metal-resin composite 100 is 280 nm or more, when the metal-resin composite 100 is used as a labeling substance for immunochromatography, stable and excellent detection sensitivity can be obtained. Here, the particle size of the metal-resin composite 100 is a value obtained by adding a length of the protrusion portion of the partially exposed particles 40 or the surface-adhered particles 50 to a particle size of the resin particle 10 and can be measured by a laser diffraction and scattering method, a dynamic light scattering method, or a centrifugal sedimentation method.

[Method of Producing a Metal-Resin Composite]

A method of producing the metal-resin composite 100 is not particularly limited. For example, a solution containing metal ions may be added to a dispersion of the resin particles 10 produced by an emulsion polymerization method, and the metal ions may be adhered to the resin particle 10 (hereinafter referred to as "metal-ion-adhered resin particles"). Further, when the metal-ion-adhered resin particles are added to a reducing agent solution, the metal ions are reduced, the metal particles 20 are generated, and the metal-resin composite 100 can be obtained.

For example, when platinum particles are generated as the metal particles 20, examples of a solution containing platinum ions include a platinum chloride acid ($H_2PtCl_6$) aqueous solution, and a platinum chloride ($PtCl_2$) solution. In addition, a platinum complex may be used in place of platinum ions.

In addition, for example, when gold particles are generated as the metal particles 20, examples of a solution containing gold ions include a chlorauric acid ($HAuCl_4$) aqueous solution. In addition, a gold complex may be used in place of gold ions.

In addition, as a solvent for the solution containing metal ions, in place of water, a hydrous alcohol such as methanol, ethanol, n-propanol, isopropanol, n-butanol, sec-butanol, and t-butanol, or an alcohol, and an acid such as hydrochloric acid, sulfuric acid, and nitric acid may be used In addition, as necessary, additives, for example, a water-soluble polymer compound such as polyvinyl alcohol, a surfactant, an alcohol; an ether such as tetrahydrofuran, diethyl ether, or diisopropyl ether; an alkylene glycol, a polyalkylene glycol, or a monoalkyl ether or dialkyl ether thereof, and a polyol such as glycerin; and various water-miscible organic solvents such as acetone and ketones, for example, methyl ethyl ketone, may be added to the solution.

Such additives are effective in increasing a rate of a reduction reaction of metal ions or controlling the size of the generated metal particles 20.

In addition, a known substance can be used as the reducing agent. Examples of the reducing agent include sodium borohydride, dimethylamine borane, citric acid, sodium hypophosphite, hydrazine hydrate, hydrazine hydrochloride, hydrazine sulfate, formaldehyde, sucrose, glucose, ascorbic acid, erythorbic acid, sodium phosphinate, hydroquinone, and Rochelle salt. Among them, sodium borohydride, dimethylamine borane, and citric acid are preferable.

As necessary, a surfactant can be added to a reducing agent solution, and a pH of the solution can be adjusted. For example, in order to adjust a pH, a buffer such as boric acid or phosphoric acid, an acid such as hydrochloric acid or sulfuric acid, and an alkali such as sodium hydroxide or potassium hydroxide can be used.

Moreover, when a reduction rate of metal ions is adjusted according to the temperature of the reducing agent solution, the particle size of the generated metal particles 20 can be controlled.

In addition, when metal ions in the metal-ion-adhered resin particles are reduced and the metal particles 20 are generated, the metal-ion-adhered resin particles may be added to the reducing agent solution, and the reducing agent may be added to the metal-ion-adhered resin particles. However, the former is preferable because the enclosed particles 30 and the partially exposed particles 40 are easily generated.

In addition, in order to maintain the dispersibility of the metal-resin composite 100 in water, for example, citric acid, poly-L-lysine, polyvinyl pyrrolidone, polyvinyl pyridine, polyvinyl alcohol, or a dispersant such as DISPERBYK 194, DISPERBYK 180, and DISPERBYK 184 (commercially available from BYK-Chemie Japan) may be added.

In addition, when a buffer such as boric acid or phosphoric acid, an acid such as hydrochloric acid or sulfuric acid, and an alkali such as sodium hydroxide or potassium hydroxide are used to adjust a pH, the dispersibility can be maintained.

The metal-resin composite 100 having the above configuration particularly allows antigens or antibodies to be adhered to the surface of the metal particles 20 and thus it can be preferably applied as a labeling substance for immunoassay, for example, EIA, RIA, CLIA, FIA, LIA, PA, ICA, HA, and HI. In addition, in particular, it can be preferably applied as a material of a labeling substance for immunological measurement or a reagent for immunological measurement which has excellent visual determination in a low concentration range (high sensitivity area). In addition, forms of a labeling substance for immunological measurement or a reagent for immunological measurement are not particularly limited. For example, a dispersion in which the metal-resin composite 100 is dispersed in water or a buffer solution with an adjusted pH can be used.

A method of adhering antigens or antibodies to the surface of the metal particles 20 is not particularly limited, and known physical attachment and chemical attachment methods can be used. A chemical attachment method is preferable because the bonding between the metal particles 20 and antigens or antibodies then becomes strong. Physical attachment and chemical attachment may be used in combination.

Examples of the physical attachment include a method in which the metal-resin composite 100 is immersed and incubated in a buffer solution containing antigens or antibodies and a method in which the metal-resin composite 100 is immersed in a buffer solution and antigens or antibodies are additionally added.

Examples of the chemical attachment include a method in which an SH group is introduced into antigens or antibodies and reacted with the metal-resin composite 100 to form a metal-SH bond and a method in which a carboxyl group is introduced on the surface of the metal-resin composite 100 and then succinimidylated to react with an amino group of antigens or antibodies to form a chemical bond. Regarding a compound for introducing a carboxyl group to the surface of the metal-resin composite 100, a compound including both a functional group having a coordination ability with respect to a metal, for example, an amino group, an SH group, carbonyl group, amide group, and imide group, and a carboxyl group is suitable. An SH group is preferable as a functional group because a coordination bond with a metal is strong, and examples of the compound having an SH group and a carboxyl group at two ends include a mercaptopropionic acid, a mercaptoundecanoic acid, and a mercaptolauric acid. In addition, a polymer compound including a plurality of functional groups having a coordination ability with respect to a metal and carboxyl groups in one molecule is likely to obtain a stable bond with the metal-resin composite 100. For example, a polyglutamic acid and a polyaspartic acid which are glutamic acid and aspartic acid polypeptides are more preferable as a polymer compound for introducing a carboxyl group to the surface of the metal-resin composite 100.

In addition, since the carboxyl group introduced to the surface of the metal-resin composite 100 is anionic, it makes a zeta potential of the metal-resin composite 100 under a basic environment negative. That is, when the carboxyl group is introduced to the surface of the metal-resin composite 100, it is possible to control a zeta potential of the metal-resin composite 100.

In the metal-resin composite 100 of the present embodiment, the characteristic behavior of the zeta potential appears because both a "cationic functional group" and an "anionic functional group" are provided on the surface of the metal-resin composite 100 (or the resin particle 10). For example, in description of a case in which a polymer constituting the resin particle 10 is a polyvinylpyridine, pyridine contained in polyvinylpyridine is a "cationic functional group" and a carboxyl group generated due to hydrolysis on the surface of the resin particle 10 or a carboxyl group introduced into the metal-resin composite 100 according to a mercaptopropionic acid treatment, a polyglutamic acid treatment, or the like is an "anionic functional group." Thus, under an acidic environment, since nitrogen in pyridine in a state of $NH^+$ is positively charged and a carboxyl group in a state of COOH is not charged, the entire surface of the metal-resin composite 100 is positively charged. On the other hand, under a basic environment, since nitrogen in pyridine in a state of N is not charged and a carboxyl group in a state of $COO^-$ is negatively charged, the entire surface of the metal-resin composite 100 is negatively charged. As a result, it is thought that the zeta potential of the metal-resin composite 100 exhibits the above first to third characteristics.

Based on the above, it is preferable to control a zeta potential in the metal-resin composite 100, for example, according to the following methods (i) to (iii).

(i) A method in which the resin particle 10 is formed of a cationic polymer (for example, a polymer to which anionic ions can be adhered) and an anionic functional group is introduced on the surface of the metal-resin composite 100 (or the resin particle 10).

(ii) A method in which the resin particle 10 is formed of an anionic polymer (for example, a polymer to which cationic ions can be adhered) and a cationic functional group is introduced on the surface of the metal-resin composite 100 (or the resin particle 10).

(iii) A method in which an anionic functional group and a cationic functional group are introduced on the surface of the metal-resin composite 100 (or the resin particle 10).

Here, examples of the "anionic functional group" include a carboxyl group, a sulfonic acid group, and a phosphonic acid group. Such anionic functional groups can be present on the surface of the resin particle 10 according to selection of a type of polymer. In addition, examples of a preferable method of introducing an anionic functional group on the surface of the metal-resin composite 100 (or the resin particle 10) include the following methods a) and b).

a) A method in which the surface of the polymer constituting the resin particle 10 is partially hydrolyzed according to an acid treatment or an alkali treatment.

Here, examples of the polymer that allows an anionic functional group to be generated due to hydrolysis include a polyester and a polyamide.

b) A method in which the metal-resin composite 100 is treated with, for example, a compound (including a polymer compound) including both a functional group having a coordination ability with respect to a metal and an anionic functional group such as the above "compound including both a functional group having a coordination ability with respect to a metal and a carboxyl group."

In addition, examples of the "cationic functional group" include a nitrogen-containing group such as a pyridinyl group and an amino group. Such cationic functional groups can be present on the surface of the resin particle 10 according to selection of a type of polymer. In addition, examples of a preferable method of introducing a cationic functional group on the surface of the metal-resin composite 100 (or the resin particle 10) include the following methods c) and d).

c) A method in which the surface of the polymer constituting the resin particle 10 is partially hydrolyzed according to an acid treatment or an alkali treatment.

Here, examples of the polymer that allows a cationic functional group to be generated due to hydrolysis include a polyamide.

d) A method in which the metal-resin composite 100 is treated with a compound (including a polymer compound) including both a functional group having a coordination ability with respect to a metal and a nitrogen-containing group.

Here, preferable examples of the "compound (including a polymer compound) including both a functional group having a coordination ability with respect to a metal and a nitrogen-containing group" include 2-aminoethanethiol, and 11-amino-1-undecanethiol hydrochloride.

Next, an analyte measurement method using the metal-resin composite 100 as a labeling substance, a test strip for lateral flow chromatography, and an analyte detection and quantification kit will be described.

[Test Strip for Lateral Flow Chromatography]

Figure 3:
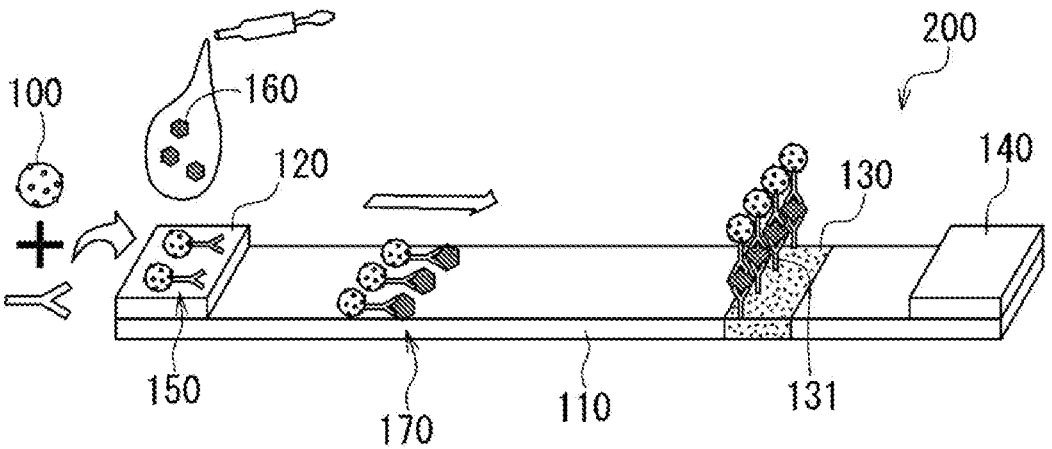
FIG. 3 is an explanatory diagram showing an overview of an analyte measurement method using a test strip for lateral flow chromatography according to an embodiment of the present invention.

First, a test strip for lateral flow chromatography (hereinafter simply referred to as a "test strip") according to an embodiment of the present invention will be described with reference to FIG. 3. As will be described below, a test strip

200 can be preferably used for an analyte measurement method according to an embodiment of the present invention.

The test strip 200 includes a membrane 110. On the membrane 110, a sample addition section 120, a determination section 130 and a liquid absorbing section 140 are provided in order in a development direction of a sample.

<Membrane>

Regarding the membrane 110 used for the test strip 200, those used as membrane materials in general test strips can be applied. The membrane 110 exhibits, for example, a capillary action, and is formed of an inactive substance (an analyte 160, a substance that does not react with various ligands) made of a microporous substance so that a sample is developed at the same time as the sample is added. Specific examples of the membrane 110 include a fibrous or nonwoven fibrous matrix, film, filter paper, glass fiber filter paper, cloth and cotton made of polyurethane, polyester, polyethylene, polyvinyl chloride, polyvinylidene fluoride, nylon, or cellulose derivatives. Among them, a film, filter paper, glass fiber filter paper and the like made of cellulose derivatives or nylon are preferably used, and a nitrocellulose film, a mixed nitrocellulose ester (a mixture containing nitrocellulose and cellulose acetate) film, a nylon film, and filter paper are more preferably used.

In order for a simpler operation, the test strip 200 preferably includes a support that supports the membrane 110. Regarding the support, for example, a plastic can be used.

<Sample Addition Section>

The test strip 200 may include the sample addition section 120 configured to add a sample containing the analyte 160. The sample addition section 120 is a section for receiving the sample containing the analyte 160 on the test strip 200. The sample addition section 120 may be formed on the membrane 110 upstream from the determination section 130 in a direction in which the sample is developed. Alternatively, a sample addition pad made of a material, for example, cellulose filter paper, glass fibers, polyurethane, polyacetate, cellulose acetate, nylon, or cotton cloth, may be provided on the membrane 110 to form the sample addition section 120.

<Determination Section>

A capture ligand 131 that specifically binds to the analyte 160 is fixed to the determination section 130. The capture ligand 131 can be used without particular limitation as long as it forms a specific bond with the analyte 160, and, for example, an antibody for the analyte 160 can be preferably used. Even if the sample is provided on the test strip 200, the capture ligand 131 is immobilized so that it cannot move from the determination section 130. The capture ligand 131 may be directly or indirectly fixed to the membrane 110 by physical or chemical bonding or adhesion, or the like.

In addition, the configuration of the determination section 130 is not particularly limited as long as a composite 170 including a labeled antibody 150 and the analyte 160 comes in contact with the capture ligand 131 that specifically binds to the analyte 160. For example, the capture ligand 131 may be directly fixed to the membrane 110, and alternatively, the capture ligand 131 may be fixed to a pad made of cellulose filter paper, glass fibers, a non-woven fabric, or the like fixed to the membrane 110.

<Liquid Absorbing Section>

The liquid absorbing section 140 is formed by a pad of a water-absorbing material, for example, cellulose filter paper, a nonwoven fabric, cloth, or cellulose acetate. A movement speed of the sample after a development front line (front line) of the added sample reaches the liquid absorbing section 140 varies depending on the material and size of the liquid absorbing section 140. Therefore, when the material and size of the liquid absorbing section 140 are selected, it is possible to set an optimal speed for detection and quantification of the analyte 160. Here, the liquid absorbing section 140 has an arbitrary configuration and may be omitted.

As necessary, the test strip 200 may further include an arbitrary unit such as a reaction section and a control section.

<Reaction Section>

Although not shown, in the test strip 200, a reaction section including the labeled antibody 150 may be formed on the membrane 110. The reaction section can be provided upstream from the determination section 130 in a direction in which the sample moves. Here, the sample addition section 120 in FIG. 3 may be used as a reaction section. When the test strip 200 includes the reaction section, if the sample containing the analyte 160 is supplied to the reaction section or the sample addition section 120, the analyte 160 included in the sample and the labeled antibody 150 can be brought into contact with each other in the reaction section. In this case, when the sample is simply supplied to the reaction section or the sample addition section 120, since it is possible to form the composite 170 including the analyte 160 and the labeled antibody 150, so-called one step type immunochromatography is possible.

The reaction section is not particularly limited as long as it includes the labeled antibody 150 that specifically binds to the analyte 160. The labeled antibody 150 may be directly applied to the membrane 110. Alternatively, the reaction section may be a section in which the labeled antibody 150 is impregnated into a pad (conjugate pad) made of, for example, cellulose filter paper, glass fibers, or a nonwoven fabric and which is fixed to the membrane 110.

<Control Section>

Although not shown, in the test strip 200, a control section in which a capture ligand that specifically binds to the labeled antibody 150 is fixed may be formed on the membrane 110 downstream from the determination section 130 in in the direction in which the sample is developed. A color development intensity is measured in the determination section 130 and also the control section. Therefore, the sample supplied to the test strip 200 is developed and reaches the reaction section and the determination section 130, and it is possible to confirm that an examination has been performed normally. Here, the control section is produced in the same manner as the above-described determination section 130 except that another type of capture ligand that specifically binds to the labeled antibody 150 is used in place of the capture ligand 131, and can have the same configuration

[Analyte Measurement Method]

Next, a method of measuring the analyte 160 according to an embodiment of the present invention that is performed using the test strip 200 will be described.

The method of measuring the analyte 160 of the present embodiment is a method of measuring the analyte 160 in which the analyte 160 included in the sample is detected or quantified. In the method of measuring the analyte 160 of the present embodiment, the test strip 200 including the membrane 110 and the determination section 130 in which the capture ligand 131 that specifically binds to the analyte 160 is fixed in the membrane 110 is used. Here, the method of measuring the analyte 160 of the present embodiment can include the following processes (I) to (III);

Process (I): a process in which the analyte 160 included in the sample is brought into contact with a labeled antibody 150 obtained by labeling an antibody that specifically binds to the analyte 160 with the metal-resin composite 100 having a structure in which the plurality of metal particles 20 are fixed to the resin particle 10, Process (II): a process in which the composite 170 including the analyte 160 and the labeled antibody 150 formed in Process (I) is brought into contact with the capture ligand 131 in the determination section 130, and Process (III): a process in which a color development intensity derived from localized surface plasmon resonance and/or light energy absorption due to electron transition of the metal-resin composite 100 is measured.

Process (I):

Process (I) is a process in which the analyte 160 included in the sample is brought into contact with the labeled antibody 150. A contact mode is not particularly limited as long as the composite 170 including the analyte 160 and the labeled antibody 150 is formed. For example, the sample may be supplied to the sample addition section 120 or the reaction section (not shown) of the test strip 200, and the analyte 160 may be brought into contact with the labeled antibody 150 in the sample addition section 120 or the reaction section, or the analyte 160 in the sample may be brought into contact with the labeled antibody 150 before the sample is supplied to the test strip 200.

The composite 170 formed in Process (I) is developed on the test strip 200 and moves and reaches the determination section 130.

Process (II):

In Process (II), in the determination section 130 of the test strip 200, the composite 170 including the analyte 160 and the labeled antibody 150 formed in Process (I) is brought into contact with the capture ligand 131. When the composite 170 is brought into contact with the capture ligand 131, the capture ligand 131 specifically binds to the analyte 160 of the composite 170. As a result, the composite 170 is captured in the determination section 130.

Here, since the capture ligand 131 does not specifically bind to the labeled antibody 150, when the labeled antibody 150 unbound with the analyte 160 reaches the determination section 130, the labeled antibody 150 unbound with the analyte 160 passes through the determination section 130. Here, when a control section (not shown) in which another capture ligand that specifically binds to the labeled antibody 150 is fixed is formed in the test strip 200, the labeled antibody 150 that has passed through the determination section 130 continues development, and binds to the other capture ligand in the control section. As a result, the labeled antibody 150 that does not form the composite 170 with the analyte 160 is captured in the control section.

After Process (II), as necessary, before Process (III), a washing process in which the test strip 200 is washed with a buffer solution that is generally used for a biochemical test, for example, water, physiological saline, or a phosphate buffer solution, may be performed. In the washing process, it is possible to remove the labeled antibody 150 (the labeled antibody 150 that is not bound to the analyte 160 and does not form the composite 170) that is not captured in the determination section 130, or the determination section 130 and the control section.

When the washing process is performed, in Process (III), if color development derived from localized surface plasmon resonance and/or light energy absorption due to electron transition of the metal-resin composite 100 in the determination section 130, or the determination section 130 and the control section is measured, it is possible to reduce a color development intensity of the background, and it is possible to increase a signal/background ratio. Therefore, it is possible to further improve detection sensitivity and quantitativeness.

Process (III):

Process (III) is a process in which a color development intensity derived from localized surface plasmon resonance and/or light energy absorption due to electron transition of the metal-resin composite 100 is measured. In Process (II) or after the washing process is performed as necessary, in the test strip 200, a color development intensity derived from localized surface plasmon resonance and/or light energy absorption due to electron transition of the metal-resin composite 100 is measured.

Here, when the control section is formed in the test strip 200, in Process (II), a composite in which the labeled antibody 150 is captured by another capture ligand is formed in the control section. Therefore, in Process (III), in the test strip 200, color development derived from localized surface plasmon resonance and/or light energy absorption due to electron transition can occur not only in the determination section 130 but also in the control section. In this manner, a color development intensity is measured in the determination section 130 and also in the control section, and thus it is possible to confirm whether the sample supplied to the test strip 200 is developed normally and has reached the reaction section and the determination section 130.

<Sample and Analyte>

The sample used in the analyte measurement method of the present embodiment is not particularly limited as long as it includes a substance that may be an antigen such as a protein as the analyte 160. For example, a biological sample including the target analyte 160 (that is, whole blood, serum, plasma, urine, saliva, sputum, a liquid wiped from the nasal cavity or pharynx, a spinal fluid, an amniotic fluid, a papillary secretion, tears, sweat, exudate from skin, fluid extracted from tissues, cells, and feces), a food extract fluid, and the like may be exemplified. As necessary, the analyte 160 included in the sample may be pretreated before the above Process (I) in order to facilitate a specific binding reaction of the labeled antibody 150 and the capture ligand 131 with the analyte 160. Here, as the pretreatment, a chemical treatment using various chemicals such as an acid, a base, and a surfactant, and a physical treatment using heating, stirring, and ultrasonic waves may be exemplified. In particular, when the analyte 160 is a substance such as an influenza virus NP antigen which is generally not exposed to the surface, a treatment using a surfactant or the like is preferably performed. As a surfactant used for this purpose, a nonionic surfactant can be used in consideration of a specific binding reaction, for example, a binding reactivity between the capture ligand 131 and the analyte 160 such as an antigen-antibody reaction.

In addition, the sample may be appropriately diluted with a solvent (such as water, physiological saline, or a buffer solution) or a water-miscible organic solvent which is used for a general immunological analysis method.

The analyte 160 is not particularly limited, and any known analyte can be used, and those having a strong anionic property, those having a strong cationic property, and others can be used. Regarding the analyte 160, for example, a tumor marker, a signal transmission substance, a protein (including polypeptides, oligopeptides, and the like), nucleic acid (including single- or double-stranded DNA and RNA, polynucleotides, oligonucleotides, PNA (peptide nucleic acid), and the like) such as a hormone, a substance including a nucleic acid, sugars (including oligosaccharides, polysaccharides, sugar chains, and the like), a substance including sugar chains, and other molecules such as lipids may be exemplified. The analyte 160 is not particularly limited as long as it specifically binds to the labeled antibody 150 and the capture ligand 131. For example, a carcinoembryonic antigen (CEA), an HER2 protein, a prostate specific antigen (PSA), CA19-9, $\alpha$-fetoprotein (AFP), an immunosuppressive acidic protein (TAP), CA15-3, CA125, an estrogen receptor, a progesterone receptor, fecal occult blood, troponin I, troponin T, CK-MB, CRP, human chorionic gonadotropin (HCG), luteinizing hormone (LH), follicle stimulating hormone (FSH), a syphilis antibody, an influenza virus human hemoglobin, a chlamydial antigen, an A group $\beta$ streptococcus antigen, an HBs antibody, an HBs antigen, rotavirus, adenovirus, albumin, and glycated albumin may be exemplified. Among them, an antigen that is solubilized by a nonionic surfactant is preferable, and an antigen that forms a self-assembly such as a virus nuclear protein is more preferable.

<Labeled Antibody>

In Process (I), the labeled antibody 150 is brought into contact with the analyte 160 included in the sample, and is used to form the composite 170 including the analyte 160 and the labeled antibody 150. The labeled antibody 150 is obtained by labeling an antibody that specifically binds to the analyte 160 with the metal-resin composite 100 having a structure in which the plurality of metal particles 20 are fixed to the resin particle 10. Here, "labeling" means that the metal-resin composite 100 is directly or indirectly fixed to an antibody by chemical or physical binding or attachment so that the metal-resin composite 100 is not detached from the labeled antibody 150 in Processes (I) to (III). For example, the labeled antibody 150 may be a substance in which the metal-resin composite 100 directly binds to an antibody or a substance in which an antibody and the metal-resin composite 100 are bound by an arbitrary linker molecule or they are fixed to insoluble particles.

In addition, in the present embodiment, the "antibody" is not particularly limited, and known antibodies can be used, and those having a strong anionic property, those having a strong cationic property, and others can be used. For example, a polyclonal antibody, a monoclonal antibody, and an antibody obtained by genetic recombination, and antibody fragments [for example, H chain, L chain, Fab, and $F(ab')_2$] having an ability to bind to an antigen and the like can be used. In addition, any of IgG, IgM, IgA, IgE, and IgD may be used as immunoglobulin. An animal species that produces an antibody may be a human or a non-human animal (for example, a mouse, rat, rabbit, goat, or horse). Specific examples of the antibody include an anti-PSA antibody, an anti-AFP antibody, an anti-CEA antibody, an anti-adenovirus antibody, an anti-influenza virus antibody, an anti-HCV antibody, an anti-IgG antibody, and an anti-human IgE antibody.

<Preferable Method of Producing Labeled Antibody>

Next, a preferable method of producing the labeled antibody 150 will be described. Production of the labeled antibody 150 can include at least the following process A;

Process A) a process in which the metal-resin composite 100 is mixed with and bound to an antibody under a first pH condition to obtain the labeled antibody 150, and preferably further includes a process B;

Process B) a process in which the labeled antibody 150 is treated under a second pH condition.

[Process A]

In the process A, the metal-resin composite 100 is mixed with an antibody under a first pH condition to obtain the labeled antibody 150. In the process A, preferably, the solid metal-resin composite 100 that is dispersed in a liquid phase is brought into contact with an antibody.

In order for the metal-resin composite 100 to be uniformly brought into contact with an antibody while dispersion of the metal-resin composite 100 and the activity of the antibody are maintained, the first pH condition is preferably a pH condition in a range of 2 to 10 and, for example, more preferably a pH condition in a range of 5 to 9. When a pH condition for binding the metal-resin composite 100 and the antibody is less than 2, the antibody may be denatured and inactivated due to strong acidity. When a pH exceeds 10, the metal-resin composite 100 and the antibody aggregate and are not easily dispersed when mixed. However, when the antibody is not inactivated due to strong acidity, a treatment is possible even at a pH below 2.

The process A is preferably performed in a binding buffer solution (binding buffer) adjusted to the first pH condition. For example, a predetermined amount of the metal-resin composite 100 is mixed into a binding buffer solution adjusted to the above pH and mixed sufficiently. As the binding buffer solution, for example, a boric acid solution adjusted to a predetermined concentration can be used. A pH of the binding buffer solution can be adjusted using, for example, hydrochloric acid, sodium hydroxide, or the like.

Next, when a predetermined amount of antibody is added to the obtained mixed solution and the solution is sufficiently stirred and mixed, it is possible to obtain a labeled antibody-containing solution. From the labeled antibody-containing solution obtained in this manner, only the labeled antibodies 150 forming a solid portion can be separated using a solid and liquid separation method, for example, centrifugation.

[Process B]

In the process B, the labeled antibody 150 obtained in the process A is treated under a second pH condition, and blocking is performed to prevent non-specific attachment to the labeled antibody 150. In this case, the labeled antibody 150 separated by the solid and liquid separation method is dispersed in a liquid phase under the second pH condition.

In order to maintain the activity of the antibody and prevent the labeled antibodies 150 from aggregating, the second pH condition is preferably in a range of, for example, pH 2 to 10. In order to prevent non-specific attachment of the labeled antibody 150, a pH is more preferably in a range of 5 to 9. When a blocking condition is a pH below 2, the antibody may be denatured and inactivated due to strong acidity. When a pH exceeds 10, the labeled antibodies 150 aggregate and are not easily dispersed.

The process B is preferably performed using a blocking buffer solution (Blocking Buffer) in which a blocking agent is adjusted to a second pH condition. For example, the blocking buffer solution adjusted to the above pH is added to a predetermined amount of the labeled antibody 150, and the labeled antibodies 150 are uniformly dispersed in the blocking buffer solution. As the blocking buffer solution, for example, a solution of a protein that does not bind to an object to be detected is preferably used. The blocking agent that can be used for the blocking buffer solution is not particularly limited and known blocking agents can be used, and those having a strong anionic property, those having a strong cationic property, and others can be used. Examples of the protein include bovine serum albumin, ovalbumin, casein, gelatin, and whey. More specifically, a bovine serum albumin solution adjusted to a predetermined concentration can be preferably used. A pH of the blocking buffer solution can be adjusted using, for example, hydrochloric acid, sodium hydroxide, or the like. When the labeled antibodies 150 are dispersed, for example, a dispersion method such as an ultrasonic treatment is preferably used. Accordingly, a dispersion in which the labeled antibodies 150 are uniformly dispersed is obtained.

In the above process A and process B, the metal-resin composite 100 is unlikely to aggregate due to pH, and can be treated in a wide pH range from acidic to alkaline. Therefore, the metal-resin composite 100 used in the present invention has an advantage that it is not easily limited by conditions for producing labeled antibodies.

As described above, the dispersion of the labeled antibody 150 is obtained. Only the labeled antibodies 150 forming a solid portion can be separated using a solid and liquid separation method, for example, centrifugation, from the dispersion. In addition, as necessary, a washing treatment and a storage treatment can be performed. The washing treatment and the storage treatment will be described below.

(Washing Treatment)

In the washing treatment, a washing buffer solution is added to the labeled antibodies 150 separated using the solid and liquid separation method, and the labeled antibodies 150 are uniformly dispersed in the washing buffer solution. For dispersion, for example, a dispersion method such as an ultrasonic treatment is preferably used. The washing buffer solution is not particularly limited. For example, a tris buffer solution, glycinamide buffer solution, and arginine buffer solution with a predetermined concentration adjusted to be in a range of pH 8 to 9 can be used. A pH of the washing buffer solution can be adjusted using, for example, hydrochloric acid, sodium hydroxide, or the like. The washing treatment of the labeled antibody 150 can be performed a plurality of times as necessary.

(Storage Treatment)

In the storage treatment, a storage buffer solution is added to the labeled antibodies 150 separated using a solid and liquid separation method and the labeled antibodies 150 are uniformly dispersed in the storage buffer solution. For dispersion, for example, a dispersion method such as an ultrasonic treatment is preferably used. As the storage buffer solution, for example, a solution obtained by adding an aggregate inhibitor and/or stabilizer with a predetermined concentration to a washing buffer solution can be used. As the aggregate inhibitor, for example, sugars represented by sucrose, maltose, lactose, and trehalose and polyhydric alcohols represented by glycerin and a polyvinyl alcohol can be used. The stabilizer is not particularly limited. For example, proteins such as bovine serum albumin, ovalbumin, casein, and gelatin can be used. In this manner, the storage treatment of the labeled antibody 150 can be performed.

In the above-described processes, additionally, as necessary, a surfactant and a preservative such as sodium azide and a paraoxybenzoic acid ester can be used.

[Analyte Measurement Kit]

The analyte measurement kit according to an embodiment of the present invention is a kit for detecting or quantifying the analyte 160 included in the sample based on, for example, an analyte measurement method of the present embodiment using the test strip 200.

The analyte measurement kit according to the present embodiment includes the membrane 110, the test strip 200 including the determination section 130 in which the capture ligand 131 that specifically binds to the analyte 160 is fixed in the membrane 110, and a detection reagent including the labeled antibody 150 obtained by labeling an antibody that specifically binds to the analyte 160 with the metal-resin composite 100 having a structure in which the plurality of metal particles 20 are fixed to the resin particle 10.

The analyte measurement kit of the present embodiment may further include other components as necessary.

When the analyte measurement kit according to the present embodiment is used, after Process (I) in which the analyte 160 in the sample is brought into contact with the labeled antibody 150 in the detection reagent is performed, the sample is supplied to the reaction section of the test strip 200 or the sample addition section 120, and Process (II) and Process (III) may be sequentially performed. Alternatively, the detection reagent is applied upstream from the determination section 130 of the test strip 200 and is appropriately dried, the reaction section is formed, the sample is then added to the formed reaction section or a position (for example, the sample addition section 120) upstream from the reaction section, and Processes (I) to (III) may be sequentially performed.

In addition, regarding applications of the metal-resin composite 100 other than the labeling substance for immunological measurement and the reagent for immunological measurement, it can be preferably applied for a solid catalyst, a dye, a paint, a conductive material, an electrode, and a sensor element.

EXAMPLES

Next, the present invention will be described in detail with reference to examples, but the present invention is not limited to such examples. Unless otherwise particularly mentioned in the following examples and comparative examples, various measurements and evaluations are as follows.

<Measurement of Absorbance of Metal-Resin Composite Particles>

The absorbance of metal-resin composite particles was measured by putting a metal-resin composite particle dispersion (dispersion medium: water) prepared to 0.01 wt % into a quartz glass cell (with an optical path length of 10 mm) and measuring the absorbance at 570 nm for a gold-resin composite and at 400 nm for a platinum-resin composite using a spectrophotometer (UV3600 commercially available from Shimadzu Corporation).

<Measurement of Concentration of Solid Content and Measurement of Supported Amount of Metal>

1 g of the dispersion whose concentration was not adjusted was put into a ceramic crucible, and was dried at 70° C. for 3 hours. The weights before and after drying were measured, and the concentration of the solid content was calculated by the following formula.

Concentration of solid content (wt %)=[weight (g) after drying/weight (g) before drying]×100

In addition, the sample after the drying treatment was additionally subjected to a heat treatment at 500° C. for 5 hours, and the weights before and after the heat treatment were measured, and the supported amount of metal was calculated by the following formula.

Supported amount of metal (wt %)=[weight (g) after heat treatment/weight (g) before heat treatment]×100

<Measurement of Average Particle Size of Resin Particles or Metal-Resin Composite Particles A disk centrifugal particle size distribution measurement device (CPS Disc Centrifuge DC24000 UHR, commercially available from CPS instruments, Inc.) was used for measurement. The measurement was performed while resin particles or metal-resin composite particles were dispersed in water.

<Measurement of Average Particle Size of Metal Particles>

An area average size of arbitrary 100 metal particles was measured from an image of a substrate produced by adding a metal-resin composite particle dispersion dropwise to a metallic mesh with a carbon support film observed under a field emission scanning electron microscope (FE-SEM; SU-9000 commercially available from Hitachi High-Technologies Corporation).

<Measurement of Zeta Potential>

A zeta potential was measured by an electrophoretic light scattering method using Zetasizer Nano-ZS (commercially available from Malvern) as a measurement device. The sample was diluted to 0.01 wt % with pure water and adjusted to each pH value in pH 3 to 10 using a hydrochloric acid or NaOH aqueous solution to prepare a measurement sample. A pH was measured using a pH meter (HORIBA LAQUA twin), and the zeta potential was then measured, and the behavior of change in the zeta potential at a plurality of pH points in pH 3 to 10 was measured. A variation width of the zeta potential was calculated from the maximum value of the zeta potential in an acidic region of pH 3 to 6, and the minimum value of the zeta potential in an alkaline region of pH 6 to 10. In addition, a linear function connecting a zeta potential at any one point at which the zeta potential was close to 0 mV and higher than 0 mV and a zeta potential at any one point at which the zeta potential was lower than 0 mV was obtained, and a pH at which the zeta potential was 0 mV, that is, a point of zero charge was calculated.

Production Example 1

<Synthesis of Resin Particles>

Trioctyl ammonium chloride (0.91 g) and polyethylene glycol methyl ether methacrylate (10.00 g) were dissolved in 300 g of pure water, and 2-vinylpyridine (48.00 g) and divinylbenzene (2.00 g) were then added thereto, and stirred at 30° C. for 50 minutes and then at 60° C. for 30 minutes under a nitrogen atmosphere. After the stirring, 2,2-azobis (2-methylpropionamidine)dihydrochloride (0.250 g) dissolved in 18.00 g of pure water was added dropwise thereto and stirred at 60° C. for 3.5 hours, and thereby resin particles A-1 with an average particle size of 371 nm were obtained. Precipitation was performed by centrifugation (9,000 rpm, 40 minutes), a supernatant was removed, dispersion was then performed again in pure water and impurities were then removed by a dialysis treatment. Then, the concentration was adjusted and a 10 wt % resin particle dispersion B-1 was obtained.

Production Example 2

<Synthesis of Resin Particles>

Resin particles A-2 with an average particle size of 439 nm and a 10 wt % resin particle dispersion B-2 were obtained in the same manner as in Production Example 1 except that 0.39 g of trioctyl ammonium chloride was used and 0.50 g of 2,2-azobis(2-methylpropionamidine)dihydrochloride was used.

Production Example 3

<Synthesis of Resin Particles>

Resin particles A-3 with an average particle size of 430 nm and a 10 wt % resin particle dispersion B-3 were obtained in the same manner as in Production Example 1 except that 1.50 g of trioctyl ammonium chloride was used, 49.50 g of 2-vinylpyridine was used, 0.50 g of divinylbenzene was used, and 0.50 g of 2,2-azobis(2-methylpropionamidine)dihydrochloride was used.

Production Example 4

<Synthesis of Resin Particles>

Trioctyl ammonium chloride (1.50 g) and polyethylene glycol methyl ether methacrylate (10.00 g) were dissolved in 300 g of pure water, 2-vinylpyridine (48.00 g) and divinylbenzene (2.00 g) were then added thereto, and stirred at 30° C. for 50 minutes and then at 60° C. for 30 minutes under a nitrogen atmosphere. After the stirring, 2,2-azobis(2-methylpropionamidine)dihydrochloride (0.250 g) dissolved in 18.00 g of pure water was added dropwise thereto and stirred at 60° C. for 3.5 hours. Then, 20 g of a sodium hydroxide aqueous solution with a concentration of 50 wt % was added thereto and stirred at 60° C. for 2 hours, and thereby resin particles A-4 with an average particle size of 312 nm were obtained. Precipitation was performed by centrifugation (9,000 rpm, 40 minutes), a supernatant was removed, dispersion was then performed again in pure water, and impurities were then removed by a dialysis treatment. Then, the concentration was adjusted and a 10 wt % resin particle dispersion B-4 was obtained.

Example 1

<Synthesis of Platinum-Resin Composite Particles>

54 g of pure water was added to B-1 (91.5 g), a 400 mM platinum chloride acid aqueous solution (100 g) was then added thereto, and stirred at 30° C. for 3 hours. The mixed solution was left for 24 hours and A-1 was then precipitated by centrifugation (3,000 rpm, 30 minutes), a supernatant was removed, and thus excess platinum chloride acid was removed. Then, the concentration was adjusted and a 5 wt % platinum ions-adhered resin particle dispersion C-1 was obtained.

Next, C-1 (20.6 g) was added to 1,392 g of pure water and 132 mM dimethylamine borane aqueous solution (40 g) was added dropwise thereto for 20 minutes with stirring at 3° C., and then stirred at 3° C. for 1 hour and at room temperature for 3 hours, and thus platinum-resin composite particles D-1 with an average particle size of 381 nm were obtained. D-1 was concentrated by centrifugation and then purified by a dialysis treatment, the concentration was adjusted, and a 1 wt % platinum-resin composite particle dispersion E-1 was obtained. The absorbance of platinum-resin composite particles F-1 in E-1 was 1.79. In addition, the average particle size of platinum particles in F-1 was 4.5 nm, and a supported amount of platinum was 36.7 wt %. The zeta potential measurement results of F-1 are shown in Table 1.

In the platinum-resin composite particles F-1, the platinum particles included enclosed platinum particles that were completely enclosed in the resin particle, partially exposed platinum particles having a portion that was embedded in the resin particle and a portion that was exposed to the outside of the resin particle, and surface-adhered platinum particles that were adhered to the surface of the resin particle, and at least some of the platinum particles were distributed three-dimensionally on the outer layer section of the resin particle. Here, 97% of the platinum particles were in a range of the first 40% from the surface of the resin particle in the particle radius in the depth direction.

Example 2

<Synthesis of Platinum-Resin Composite Particles>

A 5 wt % platinum ions-adhered resin particle dispersion C-2, platinum-resin composite particles D-2, a 1 wt % platinum-resin composite particle dispersion E-2 and platinum-resin composite particles F-2 were produced in the same manner as in Example 1 except that B-2 was used in place of B-1.

The average particle size of D-2 was 461 nm, and the absorbance of F-2 was 1.77. In addition, the average particle size of platinum particles in F-2 was 5.0 nm, and a supported amount of platinum was 37.6 wt %. The zeta potential measurement results of F-2 are shown in Table 1.

In the platinum-resin composite particles F-2, the platinum particles included enclosed platinum particles that were completely enclosed in the resin particle, partially exposed platinum particles having a portion that was embedded in the resin particle and a portion that was exposed to the outside of the resin particle, and surface-adhered platinum particles that were adhered to the surface of the resin particle, and at least some of the platinum particles were distributed three-dimensionally on the outer layer section of the resin particle.

Example 3

<Synthesis of Platinum-Resin Composite Particles>

A 5 wt % platinum ions-adhered resin particle dispersion C-3, platinum-resin composite particles D-3, a 1 wt % platinum-resin composite particle dispersion E-3 and platinum-resin composite particles F-3 were produced in the same manner as in Example 1 except that B-3 was used in place of B-1.

The average particle size of D-3 was 454 nm and the absorbance of F-3 was 1.45. In addition, the average particle size of platinum particles in F-3 was 3.8 nm, and a supported amount of platinum was 37.7 wt %. The zeta potential measurement results of F-3 are shown in Table 1.

In the platinum-resin composite particles F-3, the platinum particles included enclosed platinum particles that were completely enclosed in the resin particle, partially exposed platinum particles having a portion that was embedded in the resin particle and a portion that was exposed to the outside of the resin particle, and surface-adhered platinum particles that were adhered to the surface of the resin particle, and at least some of the platinum particles were distributed three-dimensionally on the outer layer section of the resin particle.

Example 4

<Synthesis of Gold-Resin Composite Particles>

255 g of pure water was added to B-4 (91.5 g), a 400 mM chlorauric acid aqueous solution (147 g) was then added thereto, and stirred at room temperature for 3 hours. The mixed solution was centrifuged (3,000 rpm, 30 minutes) to precipitate A-4, a supernatant was removed, and thus an excess chlorauric acid was removed. Then, the concentration was adjusted and a 2.5 wt % gold ions-adhered resin particle dispersion C-4 was obtained.

Next, C-4 (43.3 g) was added to 1,580 g of pure water and a 528 mM dimethylamine borane aqueous solution (10.0 g) was added dropwise thereto for 2 minutes with stirring at 3°

C., and then stirred at 3° C. for 1 hour and at room temperature for 3 hours, and thus gold-resin composite particles D-4 with an average particle size of 322 nm were obtained. D-4 was concentrated by centrifugation, and then purified by a dialysis treatment, and the concentration was adjusted, and a 1 wt % gold-resin composite particle dispersion E-4 was obtained. The absorbance of gold-resin composite particles F-4 in E-4 was 1.27. In addition, the average particle size of gold particles in F-4 was 30 nm, and a supported amount of gold was 53.8 wt %. The zeta potential measurement results of F-4 are shown in Table 1.

In the gold-resin composite particles F-4, the gold particles included enclosed gold particles that were completely enclosed in the resin particle, partially exposed gold particles having a portion that was embedded in the resin particle and a portion that was exposed to the outside of the resin particle, and surface-adhered gold particles that were adhered to the surface of the resin particle, and at least some of the gold particles were distributed three-dimensionally on the outer layer section of the resin particle. Here, 97% of the gold particles were in a range of the first 40% from the surface of the resin particle in the particle radius in the depth direction.

<Synthesis of Gold-Resin Composite Particles>

A 2.5 wt % gold ions-adhered resin particle dispersion C-5, gold-resin composite particles D-5, a 1 wt % gold-resin composite particle dispersion E-5 and gold-resin composite particles F-5 were produced in the same manner as in Example 4 except that B-2 was used in place of B-4.

In the gold-resin composite particles F-5, the gold particles included enclosed gold particles that were completely enclosed in the resin particle, partially exposed gold particles having a portion that was embedded in the resin particle and a portion that was exposed to the outside of the resin particle, and surface-adhered gold particles that were adhered to the surface of the resin particle, and at least some of the gold particles were distributed three-dimensionally on the outer layer section of the resin particle.

<Mercaptopropionic Acid Treatment>

E-5 (0.1 g) and a 10 mM mercaptopropionic acid aqueous solution (1.0 g) were mixed and stirred at 23° C. for 1 hour. The gold-resin composite particles F-5 were precipitated by centrifugation (12,000 rpm, 5 minutes), a supernatant was removed, and pure water (1.0 g) was then added and dispersion was performed again, an excess mercaptopropionic acid was removed, and gold-resin composite particles G-5 treated with mercaptopropionic acid were produced.

The average particle size of G-5 was 455 nm and the absorbance of G-5 was 1.36. In addition, the average particle size of gold particles in G-5 was 20 nm, and a supported amount of gold was 48.3 wt %. The zeta potential measurement results of G-5 are shown in Table 1.

Example 6

<Mercaptopropionic Acid Treatment>

Platinum-resin composite particles G-6 treated with mercaptopropionic acid were produced in the same manner as in Example 5 except that E-2 was used in place of E-5. The zeta potential measurement results of G-6 are shown in Table 1.

Example 7

<Polyglutamic Acid Treatment>

E-5 (0.1 g) and a 0.5 wt % polyglutamic acid aqueous solution (1.0 g) were mixed and stirred at 23° C. for 1 hour. Gold-resin composite particles D-5 were precipitated by centrifugation (12,000 rpm, 5 minutes), a supernatant was removed, and pure water (1.0 g) was then added thereto, and an excess polyglutamic acid was removed, and gold-resin composite particles G-7 treated with polyglutamic acid were produced. The zeta potential measurement results of G-7 are shown in Table 1.

Example 8

<Polyglutamic Acid Treatment>

Platinum-resin composite particles G-8 treated with polyglutamic acid were produced in the same manner as in Example 7 except that E-2 was used in place of E-5. The zeta potential measurement results of G-8 are shown in Table 1.

Comparative Example 1

<Synthesis of Gold-Resin Composite Particles>

A 2.5 wt % gold ions-adhered resin particle dispersion C-9, gold-resin composite particles D-9, a 1 wt % gold-resin composite particle dispersion E-9 and gold-resin composite particles F-9 were produced in the same manner as in Example 4 except that B-1 was used in place of B-4.

The average particle size of D-9 was 380 nm, and the absorbance of F-9 was 1.46. In addition, the average particle size of gold particles in F-9 was 22 nm, and a supported amount of gold was 53.7 wt %. The zeta potential measurement results of F-9 are shown in Table 1.

In the gold-resin composite particles F-9, the gold particles included enclosed gold particles that were completely enclosed in the resin particle, partially exposed gold particles having a portion that was embedded in the resin particle and a portion that was exposed to the outside of the resin particle, and surface-adhered gold particles that were adhered to the surface of the resin particle, and at least some of the gold particles were distributed three-dimensionally on the outer layer section of the resin particle.

Comparative Example 2

<Synthesis of Gold-Resin Composite Particles>

A 2.5 wt % gold ions-adhered resin particle dispersion C-10, gold-resin composite particles D-10, a 1 wt % gold-resin composite particle dispersion E-10 and gold-resin composite particles F-10 were produced in the same manner as in Example 4 except that B-2 was used in place of B-4.

The average particle size of D-10 was 455 nm, and the absorbance in F-10 was 1.36. In addition, the average particle size of gold particles in F-10 was 20 nm, and a supported amount of gold was 48.3 wt %. The zeta potential measurement results of F-10 are shown in Table 1.

In the gold-resin composite particles F-10, the gold particles included enclosed gold particles that were completely enclosed in the resin particle, partially exposed gold particles having a portion that was embedded in the resin particle and a portion that was exposed to the outside of the resin particle, and surface-adhered gold particles that were adhered to the surface of the resin particle, and at least some of the gold particles were distributed three-dimensionally on the outer layer section of the resin particle.

Comparative Example 3

<Synthesis of Gold-Resin Composite Particles>

A 2.5 wt % gold ions-adhered resin particle dispersion C-11, gold-resin composite particles D-11, a 1 wt % gold-resin composite particle dispersion E-11 and gold-resin composite particles F-11 were produced in the same manner as in Example 4 except that B-3 was used in place of B-4.

The average particle size of D-11 was 442 nm, and the absorbance of F-11 was 1.26. In addition, the average particle size of gold particles in F-11 was 16.1 nm, and a supported amount of gold was 53.9 wt %. The zeta potential measurement results of F-11 are shown in Table 1.

In the gold-resin composite particles F-11, the gold particles included enclosed gold particles that were completely enclosed in the resin particle, partially exposed gold particles having a portion that was embedded in the resin particle and a portion that was exposed to the outside of the resin particle, and surface-adhered gold particles that were adhered to the surface of the resin particle, and at least some of the gold particles were distributed three-dimensionally on the outer layer section of the resin particle.

Comparative Example 4

The zeta potential measurement results of gold colloids (Au colloid solution-SC average particle size of 50 nm commercially available from Tanaka Kikinzoku Kogyo) are shown in Table 1.

Comparative Example 5

The zeta potential measurement results of colored latex beads (carboxyl group modified-color Estapor, K1-030 Red commercially available from Merck Millipore) are shown in Table 1.

TABLE 1

| | Metal-resin composite | Zeta potential [mV] | | | Point of zero charge [pH] |
|---|---|---|---|---|---|
| | | Maximum value | Minimum value | Variation width | |
| Example 1 | F-1 | 24.7 | −58.0 | 82.7 | 5.8 |
| Example 2 | F-2 | 24.7 | −55.3 | 80.0 | 5.4 |
| Example 3 | F-3 | 37.6 | −50.9 | 88.5 | 6.1 |
| Example 4 | F-4 | 46.1 | −16.9 | 63.0 | 8.0 |
| Example 5 | G-5 | 41.5 | −36.3 | 77.8 | 6.0 |
| Example 6 | G-6 | 14.4 | −51.6 | 66.0 | 4.2 |
| Example 7 | G-7 | 23.8 | −51.3 | 75.1 | 5.6 |
| Example 8 | G-8 | 21.7 | −54.9 | 76.6 | 5.2 |
| Comparative Example 1 | F-9 | 37.1 | 8.9 | 28.2 | 12.5 |
| Comparative Example 2 | F-10 | 40.7 | 1.0 | 39.7 | 9.7 |
| Comparative Example 3 | F-11 | 31.7 | −2.6 | 34.3 | 9.6 |
| Comparative Example 4 | Gold colloid particles | −37.9 | −49.1 | 11.2 | Measurement is not possible |
| Comparative Example 5 | Colored latex beads | −11.3 | −66.9 | 55.6 | 1.8 |

Test Example 1-1

<Casein Adhesion Treatment>

A dispersion (0.1 ml) containing 1 mg of F-1 was added to a solution in which a 5 mM Tris (trishydroxymethylaminomethane) aqueous solution (0.9 ml) and casein (25 µg) were mixed and turned and stirred at 23° C. for 3 hours. Then, a supernatant solution H-1 was collected by centrifugation (12,000 rpm, 4° C., 5 min).

<Measurement of Amount of Casein Adhered>

The absorbance of H-1 at a wavelength of 280 nm was measured using a spectrophotometer, and a content of casein in H-1 was obtained according to one point calibration method using the following blank samples and standard samples. An amount of casein adhered to F-1 was calculated from the following formula. The calculated results are shown in Table 2.

Blank Sample:

A solution in which a 5 mM Tris aqueous solution (0.9 ml) and pure water (0.1 ml) were mixed Standard Sample:

A solution in which a 5 mM Tris aqueous solution (0.9 ml), casein (25 µg) and pure water (0.1 ml) were mixed (Amount of Casein Adhered to Metal-Resin Composite Particles)=(Amount of Casein Used for Casein Adhesion Treatment)−(Content of Casein in Supernatant Solution)

Test Examples 1-2 to 1-12

Amounts of casein adhered to F-2, F-3, F-4, G-5, G-6, G-7, G-8, F-9, F-10, F-11 and colored latex beads were calculated in the same manner as in Test Example 1-1 except that F-2, F-3, F-4, G-5, G-6, G-7, G-8, F-9, F-10, F-11 and colored latex beads were used in place of F-1. The calculated results are shown in Table 2. Here, regarding gold colloid, when a 1 mg/0.1 mL water dispersion was produced, since gold nanoparticles aggregated and re-dispersion was difficult, it was not possible to perform a casein adhesion treatment.

Test Example 2-1

<Whey Adhesion Treatment and Measurement of an Amount of Whey Adhered>

A whey adhesion treatment was performed on F-1 and an adhesion amount was measured in the same manner as in Test Example 1-1 except that whey was used in place of casein. An amount of whey adhered to F-1 was calculated from the following formula. The calculated results are shown in Table 3.

Blank Sample:

A solution in which a 5 mM Tris aqueous solution (0.9 ml) and pure water (0.1 ml) were mixed Standard Sample:

A solution in which a 5 mM Tris aqueous solution (0.9 ml), whey (25 µg), and pure water (0.1 ml) were mixed (Amount of Whey Adhered to Metal-Resin Composite Particles)=(Amount of Whey Used for Whey Adhesion Treatment)−(Content of Whey in Supernatant Solution)

Test Examples 2-2 to 2-12

Amounts of whey adhered to F-2, F-3, F-4, G-5, G-6, G-7, G-8, F-9, F-10, F-11 and colored latex beads were calculated in the same manner as in Test Example 2-1 except that F-2, F-3, F-4, G-5, G-6, G-7, G-8, F-9, F-10, F-11 and colored latex beads were used in place of F-1. The calculated results are shown in Table 3. Here, regarding gold colloid, when a 1 mg/0.1 mL water dispersion was produced, since gold nanoparticles aggregated and re-dispersion was difficult, it was not possible to perform a whey adhesion treatment.

TABLE 2

| Test Example | Metal-resin composite | Amount of casein adhered [μg/mg] |
|---|---|---|
| 1-1 | F-1 | 13 |
| 1-2 | F-2 | 13 |
| 1-3 | F-3 | 8 |
| 1-4 | F-4 | 17 |
| 1-5 | G-5 | 15 |
| 1-6 | G-6 | 7 |
| 1-7 | G-7 | 9 |
| 1-8 | G-8 | 8 |
| 1-9 | F-9 | 18 |
| 1-10 | F-10 | 17 |
| 1-11 | F-11 | 10 |
| 1-12 | Colored latex beads | 0 |

TABLE 3

| Test Example | Metal-resin composite | Amount of whey adhered [μg/mg] |
|---|---|---|
| 2-1 | F-1 | 20 |
| 2-2 | F-2 | 19 |
| 2-3 | F-3 | 15 |
| 2-4 | F-4 | 9 |
| 2-5 | G-5 | 11 |
| 2-6 | G-6 | 17 |
| 2-7 | G-7 | 18 |
| 2-8 | G-8 | 19 |
| 2-9 | F-9 | 5 |
| 2-10 | F-10 | 5 |
| 2-11 | F-11 | 4 |
| 2-12 | Colored latex beads | 3 |

Test Example 3

(Binding Process)

100 μg of anti-influenza type A monoclonal antibodies and 0.9 mL of a 100 mM boric acid aqueous solution (pH of 8.5) were mixed and 0.1 mL of the 1 wt % platinum-resin composite particle dispersion E-1 of Example 1 was then added thereto, and the mixture was turned and stirred at room temperature for 3 hours, and a labeled antibody dispersion J-1 containing anti-influenza type A monoclonal antibodies labeled with platinum-resin composite particles F-1 was obtained.

(Blocking Process)

Next, the labeled antibody dispersion J-1 was cooled by ice, centrifugation was then performed at 12,000 rpm for 5 and additionally the mixture was turned and stirred at room temperature for 2 hours, and a labeled antibody dispersion K-1 was obtained.

(Washing Treatment)

Next, the labeled antibody dispersion K-1 was cooled by ice, centrifugation was then performed at 12,000 rpm for 5 minutes, a supernatant was removed, 1 mL of a 5 mM Tris aqueous solution (pH 8.5) containing less than 0.1 wt % surfactant and bovine serum albumin was then added to solid residues, and a ultrasonic dispersion treatment was performed for 10 to 20 seconds. This operation was performed three times to perform the washing treatment.

(Storage Treatment)

Next, after being cooled by ice, centrifugation was performed at 12,000 rpm for 5 minutes, a supernatant was removed, 1 mL of a 5 mM Tris aqueous solution (pH of 8.5) containing less than 0.1 wt % surfactant, bovine serum albumin and 10 wt % sucrose was then added to solid residues, and a ultrasonic dispersion treatment was performed for 10 to 20 seconds, and thus a labeled antibody dispersion L-1 was obtained.

(Evaluation Using Immunochromatographic Method)

3 μl each of the labeled antibody dispersion L-1 was put into 12 wells in one row of a 96-well plate, and 100 μl of two-fold serial dilutions (from the right ×1, ×2, ×4, ×8, ×16, ×32, ×64, ×128, ×256, ×512, ×1024) of the influenza type A positive control (APC) and 100 μl of a negative control were mixed. Here, regarding the influenza type A positive control (APC), influenza type A virus inactivating antigens (commercially available from ADTEC Corporation) were diluted 100-fold using a specimen treated solution (commercially available from ADTEC Corporation) to prepare APC×1. The antigen concentration of APC×1 corresponded to 5,000 FFU/ml. The negative control was a specimen treated solution (commercially available from ADTEC Corporation).

Next, 50 μl of the mixed dispersion was put into a sample inlet having 12 holes for one row of an influenza type A evaluation monochrome screen (commercially available from ADTEC Corporation), and color development levels of test lines after 5 minutes, 10 minutes, and 15 minutes were evaluated. When a color development level after 15 minutes was 0.5 or more, it was determined as "favorable." The color development level was determined using a color sample for gold colloid determination (commercially available from ADTEC Corporation).

The immunochromatographic evaluation results of the labeled antibody dispersion L-1 are shown in Table 4.

TABLE 4

| | | Antigen dilution column | | | | | | | | | | |
|---|---|---|---|---|---|---|---|---|---|---|---|---|
| | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | 5 min | 4 | 3 | 2 | 1 | 0.5 | 0.5 | 0.1 | 0.1 | 0 | 0 | 0 | 0 |
| | 10 min | 5 | 4 | 2.5 | 1.5 | 1 | 1 | 0.5 | 0.1 | 0.1 | 0 | 0 | 0 |
| | 15 min | 5.5 | 4.5 | 3 | 2 | 1.5 | 1 | 0.5 | 0.5 | 0.1 | 0 | 0 | 0 | minutes, a supernatant was removed, 1 mL of a 5 mM Tris aqueous solution (pH of 8.5) containing 1 wt % bovine serum albumin was then added to solid residues, a ultrasonic dispersion treatment was performed for 10 to 20 seconds, Based on Table 4, it was confirmed that, in the labeled antibody dispersion L-1, a color development level after 15 minutes was 0.5 or more with respect to 128-fold diluted antigens, and favorable color development was exhibited.

Test Example 4

Immunochromatographic Evaluation of Colored
Latex

Labeled antibody dispersions J-2, K-2, and L-2 were
obtained in the same manner as in Test Example 3 except
that 1 wt % colored latex beads of Comparative Example 5
were used in place of the 1 wt % platinum-resin composite
particle dispersion E-1 of Example 1 in the binding process
of Test Example 3.

Immunochromatographic evaluation was performed in
the same manner as in Test Example 3 except that the labeled
antibody dispersion L-2 was used in place of the labeled
antibody dispersion L-1 in evaluation using an immunochro-
matographic method of Test Example 3. The results are
shown in Table 5.

selected from the group consisting of a carboxyl group,
a sulfonic acid group and a phosphonic acid group, and
the at least one cationic functional group comprises a
nitrogen-containing group, and at least a portion of the metal particles are distributed in
a planar direction and in a depth direction in each of the
resin particles in a range of the first 50% from the
surface of each of the resin particles in a resin particle
radius direction.

2. The metal-resin composite according to claim 1,
wherein, in a range of pH 3 to pH 10, a difference between
the maximum value and the minimum value of the zeta
potential is 20 mV or higher.

3. The metal-resin composite according to claim 1,
wherein a point of zero charge of the zeta potential is in
a range of pH 3.5 to pH 9.0.

TABLE 5

| | | Antigen dilution column | | | | | | | | | | | |
|---|---|---|---|---|---|---|---|---|---|---|---|---|---|
| | | APC × 1 | APC × 2 | APC × 4 | APC × 8 | APC × 16 | APC × 32 | APC × 64 | APC × 128 | APC × 256 | APC × 512 | APC × 1024 | Negative control |
| Color development level | 5 min | 0 | 0 | 0 | 0 | 0 | 0 | 0 | 0 | 0 | 0 | 0 | 0 |
| | 10 min | 0.1 | 0.1 | 0 | 0 | 0 | 0 | 0 | 0 | 0 | 0 | 0 | 0 |
| | 15 min | 0.1 | 0.1 | 0 | 0 | 0 | 0 | 0 | 0 | 0 | 0 | 0 | 0 |

Based on Table 5, it was confirmed that, in the labeled
antibody dispersion L-2 using commercially available col-
ored latex beads, with respect to 1-fold diluted antigens, the
color development level after 15 minutes was less than 0.5,
and favorable color development was not exhibited.

While embodiments of the present invention have been
described in detail above for the purpose of illustration, the
present invention is not limited to the above embodiment.

Priority is claimed on Japanese Patent Application No.
2016-256913, filed Dec. 28, 2016, the content of which is
incorporated herein by reference.

The invention claimed is:

1. A metal-resin composite comprising:
resin particles; and
a plurality of metal particles fixed to the resin particles,
wherein,
the resin particles comprise a nitrogen-containing poly-
mer selected from the group consisting of poly-2-
vinylpyridine, poly-3-vinylpyridine, and poly-4-vi-
nylpyridine,
the metal particles are particles of gold, platinum, palla-
dium, or an alloy thereof,
the metal particles comprise metal particles that are
completely enclosed in each of the resin particles,
metal particles having a portion that is embedded in
each of the resin particles and a portion that is exposed
to an outside of each of the resin particles, and metal
particles that are adhered to a surface of the resin
particles, and 20 wt % or less of the metal particles are
the metal particles that are adhered to the surface of the
resin particles,
in a range of pH 3 to pH 10, a maximum value of a zeta
potential is 5 mV or higher and a minimum value
thereof is −5 mV or lower,
at least one anionic functional group and at least one
cationic functional group are present on a surface of
each of the resin particles or the metal-resin composite,
wherein the at least one anionic functional group is 4. The metal-resin composite according to claim 1,
wherein the average particle size of the metal particles is
in a range of 1 nm to 100 nm.

5. The metal-resin composite according to claim 1,
wherein the average particle size of the metal-resin com-
posite is in a range of 30 nm to 1,000 nm.

6. A labeling substance comprising the metal-resin com-
posite according to claim 1.

7. The labeling substance according to claim 6,
wherein antigens or antibodies are adhered to the surface
of the metal-resin composite and used.

8. An immunoassay using the labeling substance accord-
ing to claim 6.

9. A reagent for immunological measurement comprising
the metal-resin composite according to claim 1.

10. An analyte measurement method for detecting or
quantifying an analyte included in a sample, the method
comprising the following Processes (I) to (III) that are
performed using a test strip for lateral flow chromatography
that includes a membrane and a determination section in
which a capture ligand that specifically binds to the analyte
is fixed to the membrane;

Process (I): a process in which the analyte included in the
sample is brought into contact with a labeled antibody
obtained by labeling an antibody that specifically binds
to the analyte with a metal-resin composite;

Process (II): a process in which a composite including the
analyte and the labeled antibody formed in Process (I)
is brought into contact with the capture ligand in the
determination section; and Process (III): a process in which a color development
intensity derived from localized surface plasmon reso-
nance and/or light energy absorption due to electron
transition of the metal-resin composite is measured, wherein the metal-resin composite includes resin particles
and a plurality of metal particles fixed to the resin
particles, the resin particles comprise a nitrogen-con-
taining polymer selected from the group consisting of
poly-2-vinylpyridine, poly-3-vinylpyridine, and poly-4-vinylpyridine, the metal particles are particles of
gold, platinum, palladium, or an alloy thereof, the metal
particles comprise metal particles that are completely
enclosed in each of the resin particles, metal particles
having a portion that is embedded in each of the resin
particles and a portion that is exposed to an outside of
each of the resin particles, and metal particles that are
adhered to a surface of the resin particles, and 20 wt %
or less of the metal particles are the metal particles that
are adhered to the surface of the resin particles, and in
a range of pH 3 to pH 10, a maximum value of a zeta
potential of the metal-resin composite is 5 mV or
higher, and a minimum value thereof is −5 mV or
lower,
at least one anionic functional group and at least one
cationic functional group are present on a surface of
each of the resin particles or the metal-resin composite,
wherein the at least one anionic functional group is
selected from the group consisting of a carboxyl group,
a sulfonic acid group and a phosphonic acid group, and
the at least one cationic functional group comprises a
nitrogen-containing group, and
at least a portion of the metal particles are distributed in
a planar direction and in a depth direction in each of the
resin particles in a range of the first 50% from the
surface of each of the resin particles in a resin particle
radius direction.
11. An analyte measurement kit for detecting or quanti-
fying an analyte included in a sample, comprising:
a test strip for lateral flow chromatography including a
membrane and a determination section in which a
capture ligand that specifically binds to the analyte is
fixed to the membrane; and
a detection reagent including a labeled antibody obtained
by labeling an antibody that specifically binds to the
analyte with a metal-resin composite,
wherein the metal-resin composite has a structure in
which a plurality of metal particles are fixed to resin
particles, the resin particles comprise a nitrogen-con-
taining polymer selected from the group consisting of
poly-2-vinylpyridine, poly-3-vinylpyridine, and poly-
4-vinylpyridine, the metal particles are particles of
gold, platinum, palladium, or an alloy thereof, the metal
particles comprise metal particles that are completely
enclosed in each of the resin particles, metal particles
having a portion that is embedded in each of the resin
particles and a portion that is exposed to an outside of
each of the resin particles, and metal particles that are
adhered to a surface of the resin particles, and 20 wt %
or less of the metal particles are the metal particles that
are adhered to the surface of the resin particles, and in
a range of pH 3 to pH 10, a maximum value of a zeta
potential is 5 mV or higher and a minimum value
thereof is −5 mV or lower,
at least one anionic functional group and at least one
cationic functional group are present on a surface of
each of the resin particles or the metal-resin composite,
wherein the at least one anionic functional group is
selected from the group consisting of a carboxyl group,
a sulfonic acid group and a phosphonic acid group, and
the at least one cationic functional group comprises a
nitrogen-containing group, and
at least a portion of the metal particles are distributed in
a planar direction and in a depth direction in each of the resin particles in a range of the first 50% from the
surface of each of the resin particles in a resin particle
radius direction.
12. A test strip for lateral flow chromatography for detect-
ing or quantifying an analyte included in a sample, com-
prising:
a membrane;
a determination section in which a capture ligand that
specifically binds to the analyte is fixed to the mem-
brane in a direction in which the sample is developed;
and
a reaction section including a labeled antibody obtained
by labeling an antibody that specifically binds to the
analyte with a metal-resin composite upstream from the
determination section,
wherein the metal-resin composite has a structure in
which a plurality of metal particles are fixed to resin
particles, the resin particles comprise a nitrogen-con-
taining polymer selected from the group consisting of
poly-2-vinylpyridine, poly-3-vinylpyridine, and poly-
4-vinylpyridine, the metal particles are particles of
gold, platinum, palladium, or an alloy thereof, the metal
particles comprise metal particles that are completely
enclosed in each of the resin particles, metal particles
having a portion that is embedded in each of the resin
particles and a portion that is exposed to an outside of
each of the resin particles, and metal particles that are
adhered to a surface of the resin particles, and 20 wt %
or less of the metal particles are the metal particles that
are adhered to the surface of the resin particles, and in
a range of pH 3 to pH 10, a maximum value of a zeta
potential is 5 mV or higher and a minimum value
thereof is −5 mV or lower,
at least one anionic functional group and at least one
cationic functional group are present on a surface of
each of the resin particles or the metal-resin composite,
wherein the at least one anionic functional group is
selected from the group consisting of a carboxyl group,
a sulfonic acid group and a phosphonic acid group, and
the at least one cationic functional group comprises a
nitrogen-containing group, and
at least a portion of the metal particles are distributed in
a planar direction and in a depth direction in each of the
resin particles in a range of the first 50% from the
surface of each of the resin particles in a resin particle
radius direction.
13. The metal-resin composite according to claim 1,
wherein all of the metal particles that are completely
enclosed in each of the resin particles are distributed in
a planar direction and in a depth direction in each of the
resin particles in a range of the first 25% from the
surface of each of the resin particles in a resin particle
radius direction.
14. The metal-resin composite according to claim 1,
wherein the resin particles further comprise divinylben-
zene and a polymerizable monomer having a charac-
teristic as a surfactant.
15. The metal-resin composite according to claim 14,
wherein the polymerizable monomer having a character-
istic as a surfactant is selected from the group consist-
ing of polyethylene glycol methyl ether methacrylate
and polyethylene glycol dimethacrylate.

* * * * *